United States Patent
Levien et al.

(10) Patent No.: US 9,638,828 B2
(45) Date of Patent: May 2, 2017

(54) METHOD AND SYSTEM FOR PERFORMING SURVEYING AND SAMPLING IN A BODY OF WATER

(71) Applicants: Louise Levien, Houston, TX (US); Amelia C. Robinson, Houston, TX (US); Robert J. Pottorf, Houston, TX (US); William E. Bond, Spring, TX (US); Aaron B. Regberg, Houston, TX (US); A Lucie N'Guessan, Houston, TX (US); Kevin T. Corbett, Missouri City, TX (US); Scott C. Hornbostel, Houston, TX (US); William P. Meurer, Magnolia, TX (US)

(72) Inventors: Louise Levien, Houston, TX (US); Amelia C. Robinson, Houston, TX (US); Robert J. Pottorf, Houston, TX (US); William E. Bond, Spring, TX (US); Aaron B. Regberg, Houston, TX (US); A Lucie N'Guessan, Houston, TX (US); Kevin T. Corbett, Missouri City, TX (US); Scott C. Hornbostel, Houston, TX (US); William P. Meurer, Magnolia, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 0 days.

(21) Appl. No.: 14/802,768

(22) Filed: Jul. 17, 2015

(65) Prior Publication Data
US 2016/0018559 A1 Jan. 21, 2016

Related U.S. Application Data

(63) Continuation-in-part of application No. 14/752,030, filed on Jun. 26, 2015.
(Continued)

(51) Int. Cl.
*G01V 8/02* (2006.01)
*B64C 39/02* (2006.01)
(Continued)

(52) U.S. Cl.
CPC .............. *G01V 8/02* (2013.01); *B63B 35/00* (2013.01); *B64C 39/024* (2013.01); *G01V 9/007* (2013.01);
(Continued)

(58) Field of Classification Search
CPC ........................................................ G01V 8/02
See application file for complete search history.

(56) References Cited

U.S. PATENT DOCUMENTS 3,899,213 A * 8/1975 Fantasia et al. ............. 250/301
5,898,373 A * 4/1999 Murad ................... G01V 15/00
340/600

(Continued)

FOREIGN PATENT DOCUMENTS

EP 0678758 10/1995
EP 2113796 11/2009
(Continued)

OTHER PUBLICATIONS

Abrams, M.A., et al., (2010), "Geochemical Evaluation of Ocean Surface Slick Methods to Ground Truth Satellite Seepage Anomalies for Seepage Detection", *AAPG Convention, Search and Discovery Article #40604*, pp. 1-18.
(Continued)

*Primary Examiner* — David Porta
*Assistant Examiner* — Hugh H Maupin
(74) *Attorney, Agent, or Firm* — ExxonMobil Upstream Research Company—Law Department

(57) ABSTRACT

Method and system is described for marine surveying. The method involves operations for exploring and developing
(Continued)

hydrocarbons with one or more unmanned vehicles. The unmanned vehicles are used to perform marine surveying and to obtain one or more samples that may be used to identify chemical, hydrocarbon and/or biologic information, which may be used for environmental monitoring of bodies of water.

35 Claims, 9 Drawing Sheets

Related U.S. Application Data

(60) Provisional application No. 62/190,999, filed on Jul. 10, 2015, provisional application No. 62/190,089, filed on Jul. 8, 2015, provisional application No. 62/180,987, filed on Jun. 17, 2015, provisional application No. 62/026,449, filed on Jul. 18, 2014.

(51) Int. Cl.
| | | |
|---|---|---|
| B63B 35/00 | (2006.01) | |
| G01V 9/00 | (2006.01) | |
| G01N 33/24 | (2006.01) | |
| G01N 33/18 | (2006.01) | |

(52) U.S. Cl.
CPC ..... *B63B 2035/008* (2013.01); *B64C 2201/12* (2013.01); *G01N 33/1833* (2013.01); *G01N 33/241* (2013.01)

(56) References Cited

U.S. PATENT DOCUMENTS

| | | | |
|---|---|---|---|
| 7,704,746 | B1 | 4/2010 | White et al. |
| 8,312,768 | B2 | 11/2012 | Duran Neira et al. |
| 8,492,153 | B2 | 7/2013 | Jones et al. |
| 8,599,382 | B2 | 12/2013 | Pierce, Jr. et al. |
| 8,883,417 | B2 | 11/2014 | Jacobs et al. |
| 9,146,225 | B2 | 9/2015 | Pottorf et al. |
| 2003/0170909 | A1 | 9/2003 | Schaumloffel |
| 2004/0037747 | A1 | 2/2004 | Sternberger et al. |
| 2007/0078610 | A1 | 4/2007 | Adams et al. |
| 2010/0042324 | A1 | 2/2010 | Murphy |
| 2011/0308790 | A1 | 12/2011 | Strapoc et al. |
| 2012/0165215 | A1 | 6/2012 | Andersen et al. |
| 2012/0204781 | A1* | 8/2012 | Chun et al. .................. 114/312 |
| 2013/0037707 | A1 | 2/2013 | Lamberti et al. |
| 2013/0116126 | A1 | 5/2013 | Ashby et al. |
| 2014/0152455 | A1 | 6/2014 | Giori et al. |
| 2014/0191893 | A1 | 7/2014 | Fox et al. |
| 2014/0378319 | A1 | 12/2014 | Regberg et al. |
| 2015/0007648 | A1 | 1/2015 | Theron et al. |
| 2015/0038348 | A1 | 2/2015 | Ashby et al. |
| 2015/0177212 | A1* | 6/2015 | Thomas et al. ............... 114/331 |
| 2015/0224502 | A1 | 8/2015 | Pargett et al. |
| 2016/0018224 | A1* | 1/2016 | Isler et al. ....................... 701/25 |

FOREIGN PATENT DOCUMENTS

| | | |
|---|---|---|
| EP | 2 273 251 | 1/2011 |
| EP | 2 584 355 | 4/2013 |
| GB | 2478511 | 9/2011 |
| KR | 20050045180 | 5/2005 |
| KR | 101313546 | 10/2013 |
| WO | 2004/025261 | 3/2004 |
| WO | 2007/008932 | 1/2007 |
| WO | WO 2013/071185 | 5/2013 |
| WO | 2013/148442 | 10/2013 |

OTHER PUBLICATIONS

ASTM International, (2011), "Standard Practices for Sampling of Waterborne Oils", pp. D4489-D4495.
Autonomous Surface Vehicles Limited, (2015), ASV Global, Retrieved Oct. 9, 2015, from C-Cat 5 Datasheet: http://www.asvglobal.com, pp. 1-4.
Caccia, M., et al., (2005), "Sampling Sea Surfaces with SESAMO", *IEEE Robotics & Automation Magazine*, pp. 95-105.
Chase, C.R., et al., (2010), "Real-Time Monitoring of Oil Using Ultraviolet Filter Fluorometry", *Sea Technology*, pp. 1-9.
Chelsea Technologies Group, Ltd., (2015), "UV AquaTracka Fluorometer", Retrieved Oct. 9, 2015 from http://www.chelsea.co.uk/allproduct/marine/fluorometers/uv-aquatracka-fluorometer, 2 pages.
CSafe Global (2015), AcuTemp AX56L, Retrieved Oct. 9, 2015 from http://www.acutemp.com/products-AcuTemp-AX56L, 1 page.
Dalgleish, F. R., et al., (2013), "Towards Persistent Real-Time Autonomous Surveillance and Mapping of Surface Hydrocarbons", *OTC 24241*, Houston: Offshore Technology Conference, pp. 1-18.
Engineering Toolbox, The, (2015) "The Engineering Toolbox—Liquids—Densities", Retrieved Oct. 9, 2015 from the Engineering Toolbox: http://www.engineeringtoolbox.com/liquids-densities-d_743.html, 8 pages.
National Oceanic and Atmospheric Administration, (2012), "Open Water Oil Identification Job Aid", Seattle: US Dept. of Commerce, pp. 1-52.
Caccia, M. et al., "Design and Exploitation of an Autonomous Surface Vessel for the Study of Sea-Air Interactions," Proceedings of the 2005 IEEE, Barcelona, Spain, pp. 3582-3587 (Apr. 2005).
Camilli, R. et al., "Integrating In-situ Chemical Sampling with AUV Control Systems," 2004 MTTS/IEEE Techno-Ocean Conf., Piscataway, NJ, pp. 101-109 (Nov. 9-12, 2004).
Chang, W.J. et al., "Evaluation of Boat Deployable Thin Film Oil Samplers," XP055216718, Offshore Technology Conf., Dallas, TX, 20 pgs. (1984).
Fries, D. et al., "Solar Robotic Material Sampler System for Chemical, Biological, and Physical Ocean Observations," XP032075878, *IEEE*, 5 pgs. (Sep. 19, 2011).
Leighton, J., "System Design of an Unmanned Aerial Vehicle (UAV) for Marine Environmental Sensing," XP055217103, S.B., http://www.dtic.mil/docs/citations/ADA573151, Massachusetts of Technology, 70 pgs. (Feb. 2013).
Robinson, B., "A Guide to the Sampling and Analysis of Waters, Wastewaters, Soils and Wastes," Environment Protection Authority, State Government of Victoria, 54 pgs. (Mar. 2000).
Aeschbach-Hertig, W., et al., (2000), "Palaeotemperature Reconstruction From Noble Gases in Ground Water Taking Into Account Equilibration With Entrapped Air", Nature, vol. 405, pp. 1040-1044.
Ballentine, C.J., et al., (2002), "Production, Release and Transport of Noble Gases in the Continental Crust", GeoScienceWorld, pp. 481-538.
Ballentine, C.J., et al., (1991), "Rare Gas Constraints on Hydrocarbon Accumulation, Crustal Degassing and Groundwater Flow in the Pannonian Basin", Earth and Planetary Science Letters, vol. 105, pp. 229-246.
Ballentine, C.J., et al., (1996), "A Magnus Opus: Helium, Neon, and Argon Isotopes in a North Sea Oilfield", Geochimica et Cosmochimica Acta., vol. 60, No. 5., pp. 831-849.
Balletine, C.J., et al., (2002), "Tracing Fluid Origin, Transport and Interaction in the Crust", GeoScienceWorld, pp. 539-614.
Battani, A., et al., (2010), "Trinidad Mud Volcanoes: The Origin of the Gas", AAPG Memoir 93, pp. 225-238.
Bell, R.J., et al., (2007), "Calibration of an In Situ Membrane Inlet Mass Spectrometer for Measurements of Dissolved Gases and Volatile Organics in Seawater", Environ. Sci. Technol., vol. 41, pp. 8123-8128.
Bosch, A., et al., (1988), "Natural Gas Association With Water and Oil As Depicted by Atmospheric Noble Gases: Case Studies From the Southeastern Mediterranean Coastal Plain", Earth and Planetary Science Letters, vol. 87, pp. 338-346.
Camilli, R., et al., (2009), "Characterizing Spatial and Temporal Variability of Dissolved Gases in Aquatic Environments With In Situ Mass Spectrometry", Environ. Sci. Technol., vol. 43, pp. 5014-5021.
Camilli, R., et al., (2007), "Characterizing Marine Hydrocarbons With In-Situ Mass Spectrometry", MTS, 7 pages.

(56) References Cited

OTHER PUBLICATIONS

Camilli, R., et al., (2010), "Tracking Hydrocarbon Plume Transport and Biodegradation At Deepwater Horizon", Science, vol. 330, pp. 201-204.
Chung, H.M., et al., (1988), "Origin of Gaseous Hydrocarbons in Subsurface Environments: Theoretical Considerations of Carbon Isotope Distribution", Chemical Geology, vol. 71, pp. 97-103.
Crovetto, R., et al., (1982), "Solubilities of Inert Gases and Methane in H2O and in D2 O in the Temperature Range of 300 to 600 K", J. Chem. Phys., vol. 78(2), pp. 1077-1086.
Dunn-Norman, S., et al., (2004), "Reliability of Pressure Signals in Offshore Pipeline Leak Detection", Dept. of the Interior, MMS TA&R Program, pp. 1-86.
Fomel, S., et al., (2007), "Poststack Velocity Analysis by Separation and Imaging of Seismic Diffractions", Geophysics, vol. 72(6), pp. U89-U94.
Heaton, T.H.E., et al., (1981), "Excess Air in Groundwater", J. Hydrol., vol. 50, pp. 201-216.
Hohl, D., et al., (2010), "Energy, Environment and Climate Directorate White Paper", DCO Energy, Environment and Climate Workshop, 38 pages.
Holbrook, W.S., et al., (2003), "Thermohaline Fine Structure in an Oceanographic Front From Seismic Reflection Profiling", Science, vol. 301, pp. 821-824.
Huc, A.Y., (2003), "Petroleum Geochemistry At the Dawn of the 21st Century", Oil & Gas Science and Technology, vol. 58(2), pp. 233-241.
IP.com, (2012), "Detection of Underwater Hydrocarbon and Related Fluid Seeps Using Reflection Seismic Data", 3 pages.
Jakuba, M.V., et al., (2011), "Toward Automatic Classification of Chemical Sensor Data From Autonomous Underwater Vehicles", IEEE/RSJ International Conference on Intelligent Robots and Systems, pp. 4722-4727.
Kharaka, Y.K., et al., (1988), "The Solubility of Noble Gases in Crude Oil at 25-100 C", Applied Geochemistry, vol. 3, pp. 137-144.
Kinsey, J.C., et al., (2011), "Assessing the Deepwater Horizon Oil Spill With the Sentry Autonomous Underwater Vehicle", IEEE/RSJ International Conference on Intelligent Robots and Systems, pp. 261-267.
Lamontagne, R.A., et al., (2001), "Response of METS Sensor to Methane Concentrations Found on the Texas-Louisiana Shelf in the Gulf of Mexico", Naval Research Laboratory, 14 pages.
Larter, S.R., et al., (1995), "Reservoir Geochemistry: Methods, Applications and Opportunities", The Geochemistry of Reservoir, Geological Society Special Publication No. 86, pp. 5-32.
Liu, W., et al., (2007), "Ternary Geochemical-Tracing System in Natural Gas Accumulation", Science in China Series D: Earth Sciences, vol. 50(10), pp. 1494-1503.
Macdonald, I.R., et al., (2002), "Transfer of Hydrocarbons From Natural Seeps to the Water Column and Atmosphere", Geofluids, vol. 2, pp. 95-107.
Makris, N.C., (2006), "Fish Population and Behavior Revealed by Instantaneous Continental Shelf-Scale Imaging", Science, vol. 311, pp. 660-663.
Mangelsdorf, K., et al., (2011), "Microbial Lipid Markers Within and Adjacent to Challenger Mound in the Belgica Carbonate Mound Province, Porcupine Basin, Offshore Ireland (IODP Expedition 307)", Marine Geology, vol. 282, pp. 91-101.
Narr, W., et al., (1984), "Origin of Reservoir Fractures in Little Knife Field, North Dakota", The American Association of Petroleum Geologists Bulletin, vol. 68(9), pp. 1087-1100.
Ozgul, E., (2002), "Geochemical Assessment of Gaseous Hydrocarbons: Mixing of Bacterial and Thermogenic Methane in the Deep Subsurface Petroleum System, Gulf of Mexico Continental Slope", Texas A&M University, Thesis, pp. 1-167.
Pinti, D.L., et al., (1995), "Noble Gases in Crude Oils From the Paris Basin, France: Implications for the Origin of Fluids and Constraints on Oil-Water-Gas Interactions", Geochimica et Cosmochimica Acta, vol. 59(16), pp. 3389-3404.
Prinzhofer, A., et al., (2003), "Gas Isotopes Tracing: An Important Tool for Hydrocarbons Exploration", Oil & Gas Science and Technology, vol. 58(2), pp. 299-311.
Ruddick, B., et al., (2009), "Waer Column Seismic Images as Maps of Temperature Gradient", Oceanography, vol. 22(1), pp. 192-205.
Sackett, W.M., (1977), "Use of Hydrocarbon Sniffing in Offshore Exploration", Journal of Geochemical Exploration, vol. 7, pp. 243-254.
Smith, S.P., et al., (1985), "Noble Gas Solubility in Water At High Temperature", GCA, vol. 46, p. 397.
Valentine, D.L., et al., (2010), "Asphalt Volcanoes as a Potential Source of Methane to Late Pleistocene Coastal Waters", Nature Geoscience, vol. 3, pp. 345-348.
Zaikowski, A., et al., (2010), "Noble Gas and Methane Partitioning From Ground Water: An Aid to Natural Gas Exploration and Reservoir Evaluation", Geology, vol. 18, pp. 72-74.
Zartman, R.E., et al., (1961), "Helium, Argon, and Carbon in Some Natural Gases", Journal of Geophysical Research, vol. 66, No. 1, pp. 277-306.
Zhang, Y., et al., (2011), "A Peak-Capture Algorithm Used on an Autonomous Underwater Vehicle in the 2010 Gulf of Mexico Oil Spill Response Scientific Survey", Journal of Field Robotics, vol. 28(4), pp. 484-496.
Dalgleish, F.R., et al., (2013), "Towards Persistent Real-Time Autonomous Surveillance and Mapping of Surface Hydrocarbons", OCT 24241, pp. 1-18.
Chase, C., et al., (2010), "Real-Time Monitoring of Oil Using Ultraviolet Filter Fluorometry", Sea Technology, pp. 45-50.
ASTM International (2011), "Standard Practices for Sampling of Waterborne Oils", Designation: D4489-95 (Reapproved 2011), pp. 1-4.

\* cited by examiner

METHOD AND SYSTEM FOR PERFORMING SURVEYING AND SAMPLING IN A BODY OF WATER

CROSS-REFERENCE TO RELATED APPLICATION

This application claims the benefit of U.S. patent application Ser. No. 14/752,030 filed Jun. 26, 2015; U.S. Provisional Patent Application Ser. No. 62/026,449 filed Jul. 18, 2014; U.S. Provisional Patent Application 62/180,987 filed Jun. 17, 2015; U.S. Provisional Patent Application 62/190,089 filed Jul. 8, 2015; and U.S. Provisional Patent Application 62/190,999 filed Jul. 10, 2015, the entirety of each is incorporated by reference herein.

FIELD OF THE INVENTION

The present techniques relate generally to the field of marine surveying and sampling. Specifically, the present techniques relate to sampling operations for chemical, hydrocarbon and biologic information. This information may be used for hydrocarbon exploration, hydrocarbon development, and/or environmental monitoring of bodies of water with one or more unmanned vehicles. These vehicles may be directed based on instructions or commands from operators, which are land-based, air-based, or ship-based, or directed by onboard instrumentation that responds to signals generated when certain biology, hydrocarbons and/or chemicals are present in the body of water.

BACKGROUND

Conventional marine surveying is performed in a variety of approaches. One marine surveying approach involves the use of manned vessels or vehicles to collect samples. See, e.g., American Standards and Testing Association's Standard Practice D4489. However, such sampling approaches are expensive due to the vessel deployment requirements and the number of samples is limited by the amount of time a vessel and its crew can remain on the body of water to perform operations. Further, samples obtained from the manned vessel's operations may fail to obtain samples from a target of interest or include samples that are compromised due to marine vessel traffic or other disturbances. As a result, the conventional approaches may provide a limited coverage area, may require certain amounts of lead time to prepare and deploy the vessel and crew, may involve additional verification steps to confirm a target of interest is present because of the delays in deployment, and may provide limited flexibility for adjusting a course plan or trajectory during operations (e.g., real-time or concurrent adjustments). As such, manned marine surveying approaches have various limitations for surveying operations.

Another marine surveying approach may involve using monitoring equipment coupled to a buoy. This approach may be utilized to obtain different types of measurements, such as temperature, wind speed, current, or basic water chemistry from a location. However, such approaches are not particularly useful for acquiring samples for sophisticated measurements or advanced characterization, which may involve land-based laboratory analysis. Specifically, the buoys merely provide instantaneous information from a static location, and may only capture discrete samples (if at all). The use of buoys does not provide a means to adjust the buoys position to intercept a potential target, a means to provide geochemical data confirming the presence of target materials, a means to reserve the sampling apparatus for capturing representative samples of the chemical, hydrocarbon and/or biological target, or a means to ascertain target presence and abundance in the area of interest. In addition, identifying temporal and spatial variation of targets is implausible, given that the number and distribution of buoys is limited and may not provide needed information, such as geochemical information or sampling resolution necessary to capture specific conditions, target compositions, or transformations that may occur within the water column or at the water surface (e.g., evaporation and/or ultraviolet induced degradation). As such, the monitoring equipment approaches have various limitations in performing surveying operations.

Yet another approach for marine surveying may include remote sensing coupled with a sampling operations. This approach may be used to identify possible features of interest (e.g., oil slicks from seeps, red tide or a chemical pollutant) or wildlife (e.g., invasive, rare, threatened or endangered species locations). The remote sensing may be performed indirectly (e.g., with satellite or airborne imaging) or directly (e.g., via observations and sampling from a marine vessel). Then, a marine vessel can be deployed with a manned crew to determine the location of the observation and to obtain samples. However, similar to the discussion above regarding manned approaches, the deployment of a marine vessel may be time consuming and expensive to operate. Further, because the deployment involves processing remote sensing data and the deployment may involve delays, this approach may not be able to locate the ephemeral feature, as it is not performed in a timely manner. That is, the target or feature may have aged, dissipated, or moved to a different location as a result of changes in conditions, such as currents and/or wind. In addition, a chemical associated with the target may have to involve high concentrations to be detected and may have to be at the surface to be discernable via satellite or aircraft. Also, this approach may have difficulties in addressing and overcoming limitations from noise (e.g., signal to noise ratio in processing of the data). These difficulties may be a result of the problems of determining background levels present within a certain body of water and identifying anomalies as compared to the background levels, and then to locate anthropogenic sources that may not persist over time. Thus, this approach has additional limitations.

As a result, enhancements to marine surveying approaches are needed. In particular, marine surveying may include obtaining samples of biological, hydrocarbons and/or chemicals, which may be used to enhance hydrocarbon exploration, hydrocarbon development, and/or environmental monitoring of bodies of water with one or more unmanned vehicles. The obtained samples may also provide biodiversity data at different trophic levels, through the analysis of environmental deoxyribonucleic acid (eDNA), which may provide useful information on the impact of an event or ongoing anthropomorphic features, for waterborne pathogens and for studying invasive or endangered species.

SUMMARY

In one or more embodiments, a method for performing a marine survey is described. The method includes (a) transporting a plurality of sample containers on an unmanned vehicle to a potential location of target material in a body of water, wherein the target material comprises one or more of biological, chemical, hydrocarbons and any combination thereof and wherein the unmanned vehicle is one of unmanned surface vehicle and an unmanned airborne vehicle; (b) obtaining a sample of the target material; (c) disposing the obtained sample into one of the plurality of sample containers on the unmanned vehicle; and (d) repeating the steps (b) to (c) for another sample, wherein the obtained samples are stored in individual sample containers of the plurality of sample containers. The method may further include determining whether the obtained sample is associated with a hydrocarbon system and/or determining whether the obtained sample is associated with chemical or biological materials. Further still, the method may include identifying an additional sampling location to obtain one or more of sediment samples, biological samples, chemical samples, other non-hydrocarbon samples and any combination thereof; directing the unmanned vehicle to the identified additional sampling location; obtaining one or more samples at the identified additional sampling location; and analyzing the obtained sample for geochemical or biological materials.

In one or more embodiments, a marine target identification system is described. The system may include an unmanned vehicle having a propulsion component, a communication component and a sample component, wherein the propulsion component is configured to maneuver the unmanned vehicle, the sample component is configured to obtain one or more samples of a target material and the communication component is configured to communicate signals associated with the obtained samples, wherein the target material comprises one or more of biological, chemical, hydrocarbon and any combination thereof and wherein the unmanned vehicle is one of unmanned surface vehicle and an unmanned airborne vehicle. Further, the target material comprises one or more of biological, chemical, hydrocarbon and any combination thereof.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION

Figure 1:
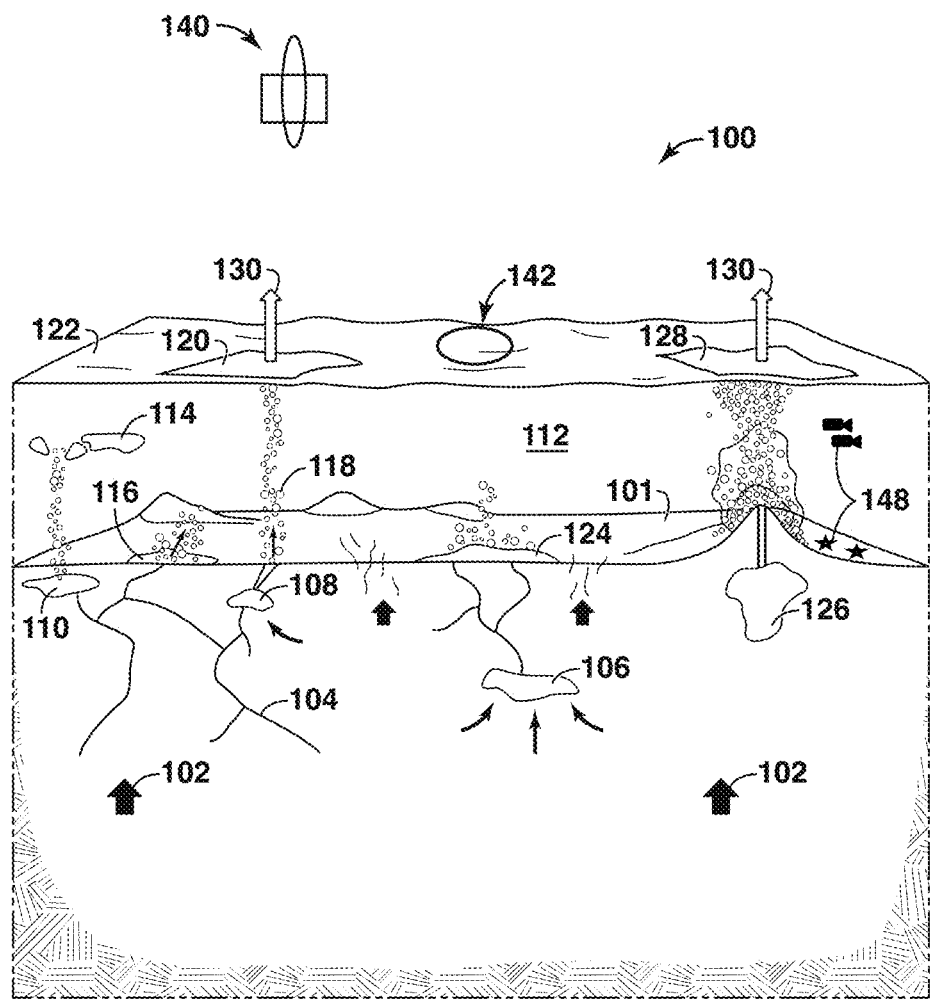
FIG. 1 is a side elevational view of an exemplary diagram having a body of water floor, a body of water and air above the body of water.

In the following detailed description section, the specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the present disclosure is not limited to the specific embodiments described below, but rather, it includes all alternatives, modifications, and equivalents falling within the true spirit and scope of the appended claims.

Various terms as used herein are defined below. To the extent a term used in a claim is not defined below, it should be given the broadest definition persons in the pertinent art have given that term as reflected in at least one printed publication or issued patent.

The articles "the", "a" and "an" are not necessarily limited to mean only one, but rather are inclusive and open ended so as to include, optionally, multiple such elements.

As used herein, "marine", means any body of water. The bodies of water may include oceans, seas, gulfs, lakes, rivers and streams, for example.

As used herein, the term "hydrocarbon system" refers to the relationships between required components and the processes required for the presence of any subsurface hydrocarbon accumulation as described by Magoon and Beaumont. See, e.g., Magoon and Beaumont, The Petroleum System—from source to trap: AAPG Memoir 60 (1994). Subsurface hydrocarbon accumulations in a sedimentary basin include (1) the presence of a source rock from which hydrocarbons can be generated, (2) the burial of the source rock to sufficient temperatures and pressures to result in the generation and expulsion of liquid hydrocarbons from a source rock (source maturity), (3) presence of a reservoir of sufficient adequacy to store hydrocarbons, (4) migration of liquid hydrocarbons to and accumulation in a reservoir, and (5) a trap and a seal that prevents significant leakage of hydrocarbons from the reservoir. The relative timing of each of these components and processes are utilized to determine the existence of any accumulation.

As noted above, marine surveying, and in particular environmental sampling, is difficult to perform and has various limitations with conventional approaches. For example, the conventional manned surveying approach of sampling a body of water requires the use of a manned marine vessel on which personnel visually locate the area of interest and then use various methods to manually collect a sample. This sampling approach is expensive because of personnel expenses, as it involves lengthy deployments to collect samples. Further, many of the locations of interest may be in remote locations that are long distances from major ports and other marine vessels (e.g., vessels of opportunity). The remote nature of these locations increases the cost of the required manned vessel operations.

The present techniques provide enhancements to marine surveying (e.g., hydrocarbon exploration, hydrocarbon development, environmental assessment and/or surveying techniques), which utilizes one or more unmanned vessels to collect samples. The unmanned vessel may be used concurrently with the performance of remote sensing over a region to identify potential locations of target materials (e.g., potential biological, chemical and/or hydrocarbon locations). Also, the unmanned vessel may be used to collect samples from the locations on the body of water. Because underwater vehicles may be subjected to limitations with power usage and/or communications, the unmanned vehicle (UV) may preferably be an unmanned surface vehicle (USV) and/or unmanned airborne vehicle (UAV). The concurrent operations may include obtaining and transmitting the remote sensing data or information derived from the remote sensing data to one or more unmanned vehicles. Then, one or more of the unmanned vehicles may be deployed to the location (e.g., biological, chemical and/or hydrocarbon location) for sampling operations.

In the present techniques, the remote sensing data is acquired, interpreted and communicated in near real-time or concurrently. The term, "near real-time", means that information is obtained, processed, and acted upon prior to UV deployment (e.g., one or two weeks prior to UV deployment) and/or during the UV deployment. The term includes time delay between the acquisition of the remote sensing data and the time at which such data can be acted upon. The transmitted location may be used to guide the UV to any identified location (e.g., suspected biological, chemical and/or hydrocarbon location) for sampling. The term, "concurrent" or "concurrently", means that the information is obtained, processed, and acted upon at time intervals that overlap with each other. That is, the acquisition, processing and transmission of the remote sensing data may be performed within a first time interval and the UV may be performing operations for a second time interval (e.g., performing the deployment stage, sampling stage, etc.). The first time interval and the second time interval overlap during the performance of the method.

Beneficially, such techniques provide enhancements over conventional approaches. For example, environmental information is typically not obtained for a regional scale, not appropriately evaluated or sampled and may not be integrated with hydrocarbon information. Also, the present techniques combine remote sensing with UV sampling to create a less expensive means of evaluating target materials, such as hydrocarbons, biodiversity and water body chemistry.

In one or more embodiments, the present techniques utilize a combination of satellite and/or airborne remote sensing techniques along with an unmanned vehicle to characterize and map the body of water in concurrent operations. The combination of remote sensing techniques along with an unmanned vehicle that obtains samples provides a more detailed characterization of the environmental features of the marine environment over many different scales. The data collected may include one or more of biological, chemical, or hydrocarbon data and any combination thereof.

The remote sensing operations (e.g., satellite and/or airborne) may include synthetic aperture radar (SAR) along with other techniques. Remote sensing involves obtaining measurements over the body of water. As an example, remote sensing refers to the use of sensors mounted on orbiting satellites to acquire synthetic aperture radar (SAR) images and/or other types of data that indicate the area of interest. The remote sensing data may be integrated with other data to further enhance the process and provide different scales of information about a region of interest. For example, the remote sensing data may be combined with measurement data, which may be provided from a marine vessel (e.g., vessels performing other duties such as seismic and acoustic imaging, multibeam echosounder, side-scan sonar, sub-bottom profiler; magnetic and gravity surveying) and sampling data from the unmanned vehicle.

The sampling is performed by an unmanned vehicle (UV), such as an unmanned surface vehicle (USV) or unmanned airborne vehicle (UAV). The UV may include autonomous control or may be remotely operated. The UV may include one or more modules or components configured to perform various tasks, such as acquiring samples and/or detecting chemical, biological or physical anomalies, which may indicate changes in environmental factors. For example, the UV may include a detection module, sampling module, propulsion module and communication module.

In one or more embodiments, the present techniques may be used to perform enhanced marine surveying. The method may include obtaining a potential location of target materials using remote sensing data, acoustic measurements, shipboard measurements or other similar data; directing an unmanned vehicle (e.g., UAV or USV) to the potential location (e.g., biological, chemical and/or hydrocarbon location); and obtaining a sample of target materials (e.g., water, biological material, chemicals, hydrocarbons and/or other target materials) with the unmanned vehicle. The method may include performing remote sensing (e.g., synthetic aperture radar (SAR)) in a survey area to identify the potential location to sample.

In yet other embodiments, the present techniques provide an enhanced marine surveying method that obtains information for biodiversity at different trophic levels, through analysis of environmental deoxyribonucleic acid (eDNA) (e.g., environmental assessment and monitoring). The present techniques may provide useful information on various environmental features, including biodiversity, chemistry, and ambient physical properties. As one embodiment, a region of interest may be identified, which may be a location of planned activities, current operations, and/or event location. The UV may obtain water or sediment samples along with a particular chemical, hydrocarbon and/or biological (including environmental DNA) target.

Moreover, in one or more embodiments, the present techniques may include performing a surveying by obtaining baseline environmental data (e.g., biological, chemical and/or hydrocarbon data) at different times periods to monitor an area. The method may include obtaining target materials for an identified location (based on remote sensing or planned operations); directing an unmanned vehicle (e.g., UAV or USV) to the identified location (e.g., biological, chemical and/or hydrocarbon location); and obtaining a sample of target materials (e.g., water, biological material, chemicals, hydrocarbons and/or other target materials) with the unmanned vehicle. This process may be repeated for different time periods (e.g., separated by a week, a month, a year or three year period) to form a time related sequence of data for the location. For example, the different sampling operations may be performed in different months, different years and/or other suitable periods of time.

Further, certain embodiments may include performing marine surveys, which involves initial assessments or ongoing monitoring. The marine surveying may involve biological characterization of an area of interest and may include species detection, habitat mapping, and ecosystem health evaluation. Species detection may identify the presence and distribution of specific biologic targets (e.g., microbial populations, plankton diversity, or fish diversity), whereas habitat mapping may overlay distributions of different biological targets as a function of various physical features of the area of interest. The biological targets for habitat mapping may also utilize distributions of organisms that are typically associated with the target of interest to define habitat boundaries. For example, the method may include habitat mapping for whales, however, whale habitats or possible habitats may be defined or limited by the distribution of sources of whale food. Further, habitat mapping and changes in habitat characteristics over time may provide additional understanding for the ecosystem's health. To fully evaluate the ecosystem's health, physical and chemical indicators may be combined with the biological parameters associated with environmental conditions. For example, dragon flies tend to be associated with bodies of water that maintain a particular range of physical and chemical properties. The absence of dragon flies from an area that was previously populated by dragonflies may be an indirect indication of changes in the water's physical and chemical properties. Accordingly, the surveying may involve monitoring physical or chemical aspects of an environment, such as water quality of fluvial systems or coastal margins. The survey may monitor transitions associated with perturbations in the geosphere, hydrosphere, or biosphere.

Further still, in some other embodiments, the present techniques may include two or more unmanned vehicles. For example, the present techniques may include transporting and/or storing one or more sample containers on a first or deployment unmanned vehicle (e.g., UAV or USV). The first unmanned vehicle may be configured to measure and collect the samples, but the samples may be stored in a second or storage unmanned vehicle. The second unmanned vehicle may return to the deployment location to deliver the samples and to re-stock with unused sample containers, while the first UV may continue to operate. Various aspects of the present techniques are described further in FIGS. 1 to 11.

FIG. 1 is a side elevational view of an exemplary diagram 100 having a body of water floor 101, a body of water (e.g., ocean 112) and air above the body of water. This diagram 100 illustrates various target materials, such as waterborne liquid hydrocarbons 120 and 128 and aquatic organisms 148, in a marine or aquatic environment. The detecting and acquiring of the target material may be performed via a remote sensing unit 140 and unmanned vehicle 142.

For the hydrocarbons, numerous subsurface sources and migration pathways of hydrocarbons are present at or result in hydrocarbons escaping from seeps on the body of water floor, such as ocean floor 101. Hydrocarbons 102 generated at source rock (not shown) migrate upward through faults and fractures 104. The migrating hydrocarbons may be trapped in reservoir rock and form a hydrocarbon accumulation, such as a gas 106, oil and gas 108, or a gas hydrate accumulation 110. Hydrocarbons seeping from the gas hydrate accumulation may dissolve into methane and higher hydrocarbons (e.g., ethane, propane) in the ocean 112, as shown at feature 114, or may remain as a gas hydrate on the ocean floor 101, as shown at feature 116. Alternatively, oil or gas from oil/gas reservoir 108 may seep into the ocean, as shown at feature 118, and form target materials (such as waterborne liquid hydrocarbons 120) on the ocean surface 122. A bacterial mat 124 may form at a gas seep location, leaking from gas reservoir 106, and may generate biogenic hydrocarbon gases, while degrading thermogenic wet gas. Still another process of hydrocarbon seepage is via a mud volcano 126, which can form waterborne liquid hydrocarbons 128 on the ocean surface. Target material (such as waterborne liquid hydrocarbons 120 and 128 or methane gas 130 (and e.g., ethane, propane, etc.)) emitted therefrom are signs of hydrocarbon seepage that are, in turn, signs of possible subsurface hydrocarbon accumulation.

In addition to the hydrocarbons, the ocean floor 101 and ocean 112 may include various chemicals and biology. For example, the ocean 112 may include various aquatic organisms 148 (e.g., bacterial mats, fish, starfish, whales and the like). The remote sensing unit 140 may detect schools aquatic organisms 148 and the unmanned vehicle 142 may record or sample biologic and/or chemical materials in the ocean 112.

The signatures measured from each of the target materials (e.g., seeps) may be analyzed according to methodologies and techniques disclosed herein to provide information about the environment (e.g., a hydrocarbon system). For example, for seeps, the information may be used to provide information about the environment. For example, for seeps the information may be used to discriminate between the different origins of hydrocarbons encountered at these seeps. In particular, methodologies and techniques disclosed herein may discriminate between hydrocarbons that have migrated directly to the surface without encountering a trap within which they can be accumulated (e.g., a first source) and hydrocarbons that have leaked from a subsurface accumulation (e.g., a second source). If the presence and volume of such a hydrocarbon accumulation can be identified, it is possible the hydrocarbons from such an accumulation can be extracted. Further, the present techniques may be utilized to obtain biological and chemical data about the ocean floor 101 and ocean 112, as well. For example, the present techniques may discriminate among the presence of different aquatic organisms 148, which may be utilized to indicate different aspects about the ocean 112.

To enhance the surveying operations, the remote sensing unit 140 and unmanned vehicle 142 may detect and acquire various target materials. In this diagram 100, the remote sensing unit 140 is a satellite that is collecting data regarding the ocean surface 122 and/or may also provide data about objects on or near the surface of the water as well as within the body of water, such as ocean 112. The remote sensing unit 140 is utilized to process the acquired data and provide an indication of identified target materials at identified locations, such as waterborne liquid hydrocarbons 120 and 128. Then, the locations of the target materials are communicated to the unmanned vehicle, which is an unmanned surface vehicle (USV) 142 in this diagram 100. The USV 142 may then move to a location near each of the target locations to obtain samples (e.g., waterborne liquid hydrocarbons 120 and 128 to obtain samples of the hydrocarbons at the location). These samples may be stored and then analyzed to determine if the target materials are associated with hydrocarbon seeps. Further, the unmanned vehicle 142 may also move to a location near aquatic organisms 148 to obtain samples of biology or chemistry. These samples may be stored and then analyzed, for example, to determine biodiversity of the area associated with hydrocarbons seeps and/or identified location.

As may be appreciated, natural seepage, aquatic organisms and/or chemistry of the ocean are often episodic, which makes the collection of samples of a target material difficult. A satellite image may indicate the likely presence of a target material, such as waterborne liquid hydrocarbons or aquatic organisms, but at a later time period (e.g., hours later) the waterborne liquid hydrocarbons may have dissipated and/or aquatic organisms may have migrated and may be undetectable upon arrival. For example, an area over a few square kilometers may have fairly consistent seepage, but the precise locations of the seeping origins and their waterborne liquid hydrocarbons may vary due to the meteorological or other environmental conditions.

As a result, the target materials, such as waterborne liquid hydrocarbons or aquatic organisms, identified by satellite may be sporadic and not have a continuous presence for any considerable length of time. The UV provides the ability to confirm the presence of the target prior to collecting a sample at its location with some confidence. Without this ability, there is a high likelihood that a vast majority of the samples collected may contain no significant amount of target materials (e.g., hydrocarbons, biologic materials and/or chemical materials). As such, the UV may have to spend considerable amounts of time searching for the target material (e.g., potential seepage locations and/or aquatic organisms).

To assist the UV, remote sensing may be utilized, such as SAR technology. SAR images may be obtained for substantial amounts of the area of interest at different intervals. For example, the intervals may be two days, although the frequency of acquisition, resolution of images, and size and location of images may be adjusted for different applications. Once analyzed, commands are issued to the UV, as appropriate, based at least partially on the information obtained from the SAR images. The method associated with one exemplary method is further described in FIG. 2.

Figure 2:
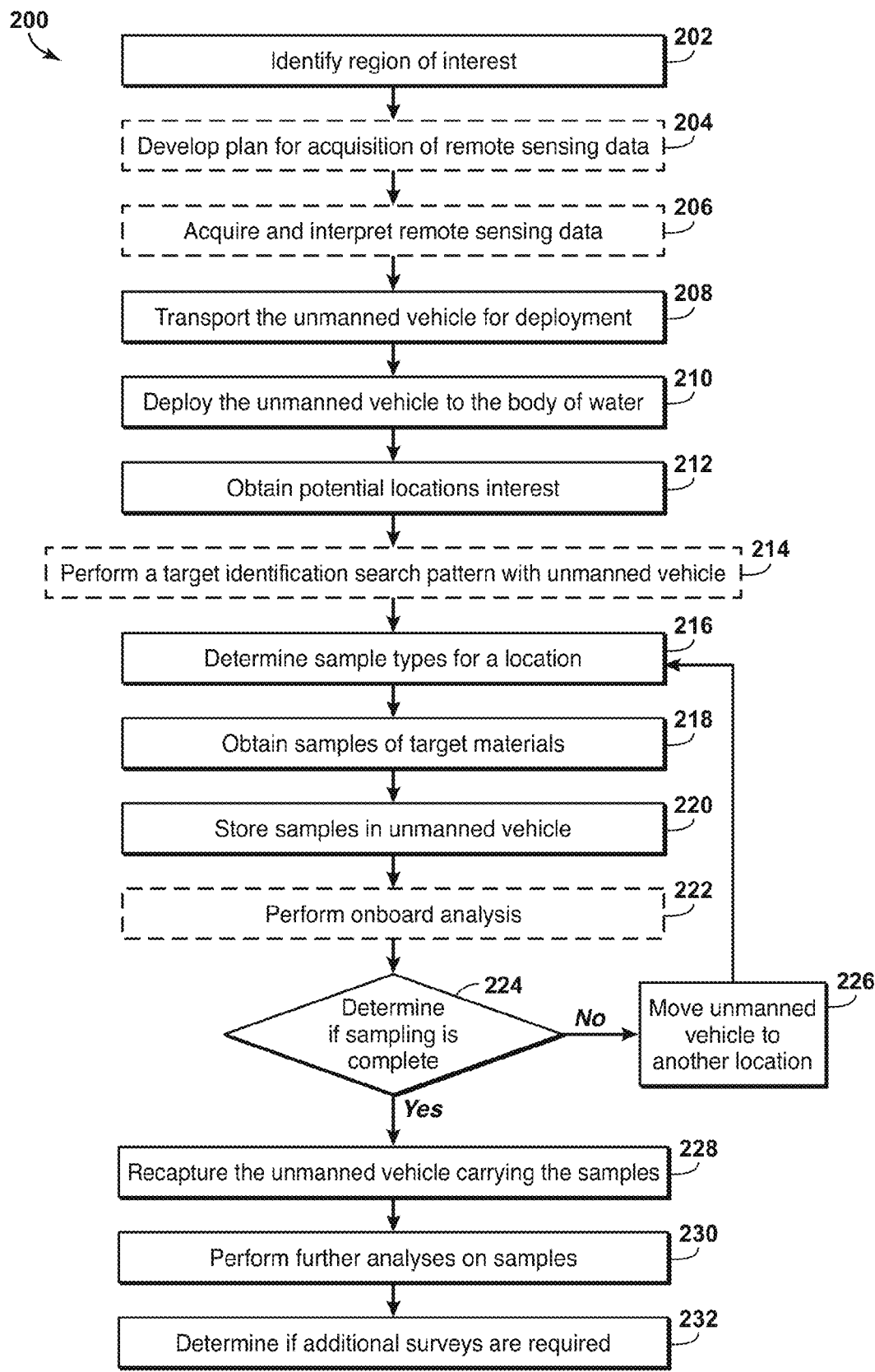
FIG. 2 is a flow chart for using remote sensing along with an unmanned vehicle to perform marine surveying in accordance with an exemplary embodiment of the present techniques.

FIG. 2 is a flow chart 200 for using an unmanned vehicle to perform marine surveying in accordance with an exemplary embodiment of the present techniques. In this flow chart 200, various blocks relate to identifying a region of interest, such as blocks 202 to 206, which may be referred to as the identification stage. Other blocks involve a searching stage, as shown in blocks 208 to 214, and a sampling stage, as shown in blocks 216 to 226. Finally, blocks 228 to 232 relate to further operations stage that may include collecting the unmanned vehicle and may include further analysis of samples that may be useful for certain environmental analysis operations.

The identification stage is described in blocks 202 to 206. At block 202, a region of interest is identified. The identification of a region of interest (e.g., area of interest) may include performing various operations prior to deployment of the UV via remote sensing. The remote sensing survey may include satellite imagery and airborne surveys. The remote sensing techniques may include synthetic aperture radar (SAR) images and/or other types of data that indicate the presence of target material. For example, the identification of a region of interest may include identification of a region of interest for study related to the biodiversity of the area, studying the water chemistry of a region of interest, identifying the extent of an algal bloom or other feature that may interrupt food supplies, fingerprinting a specific compound to determine its source or any other reason that sampling of fluids or sediments may be useful. The remote sensing data or information may be used to identify areas (e.g., regions of interest) that have a higher probability of being of useful for the survey. Then, additional data for the area of interest, such as wind direction and velocity for calculating potential movements over time, may be analyzed to further refine and verify the locations of interest. At block 204, a plan for acquisition of remote sensing data may optionally be developed. The plan for acquisition of remote sensing data may be developed before or during the UV deployment (e.g., concurrently with UV deployment). For example, the UV deployment plan may be developed after reviewing any obtained data regarding the regions of interest. This may involve planning to acquire additional concurrent data for the area of interest, which may be prior to UV deployment and continuing for the duration of the UV deployment. At block 206, the remote sensing data may optionally be acquired and interpreted. The remote sensing data (e.g., SAR data) may be obtained prior to and/or concurrently with the UV deployment operations (e.g., during UV deployment). The remote sensing data may not need to be obtained if the region of interest is known or has been identified from other sources.

With the identified region or area of interest, the exploring for the target material in a searching stage is performed in blocks 208 to 214. At block 208, the UV is transported for deployment. It may be deployed from shore or may be transported to the area of interest by a deployment vessel. The deployment vessel may include a marine vessel or an airborne vessel that is capable of transporting the UV to a location in or near the body of water. Prior to deployment into the body of water, the UV is loaded with the appropriate sensors, sampling containers and other equipment that may be utilized for collection of different types of samples. Then, at block 210, the UV is deployed to the body of water. The deployment of the UV may include preparing the UV for operations and beginning the operations of the UV. Once deployed, the UV obtains a potential location of interest, as shown in block 212. The potential region of interest may be based on the remote sensing data and/or may be a region identified for analysis (e.g., delineated as a habitat or region for analysis). The communication of the location may be directly to the unmanned vehicle and/or may be with a control unit that communicates with the unmanned vehicle. The control unit may be located on a marine vessel, airborne vessel or land-based location that communicates with the unmanned vehicle. Further, the communication of the location of interest may include directional information, global positioning system coordinates and/or other suitable information to indicate the location of the area of interest. At block 214, the unmanned vehicle may perform a target identification search pattern. The target identification search pattern may include performing a screening search pattern to high-grade the sampling area, identifying additional information about the area (e.g., from images or photos, sonic detection of fauna or flora, or other measurements), and/or to confirm that the identified area of interest has the target material. The search pattern may include moving the unmanned vehicle to the potential location, which may be one of various potential locations identified from the remote sensing stage or a region identified for analysis (e.g., planned for future development or operations and/or location of current development and/or operations). Once at the location, a search pattern may be performed to locate the area of interest. As part of performing a search, the UV may utilize one or more measurement components (e.g., sensors) to locate the area of interest or target material. For example, the sensors may include ultrasound measurements, analyzing the water to detect hydrocarbons, visible images to detect large mammals or schools of fish; deploying a unmanned vehicle (e.g., balloon or other airborne vehicle above the USV to obtain and analyze electromagnetic radiation data (e.g., infrared and visible light data) to identify the fauna, flora and/or waterborne hydrocarbons; and/or deploying an unmanned aerial vehicle (UAV) with cameras or other sensors to identify target material (e.g., hydrocarbons, plants and/or animals present in the area). The use of the unmanned airial vehicle (e.g., a balloon) may include deploying an unmanned airial vehicle above the USV, wherein the unmanned airial vehicle has electromagnetic radiation module (e.g., infrared and visible light detection components); obtaining electromagnetic radiation images (e.g., infrared and visible light images) for the region around the USV and analyzing the electromagnetic radiation images (e.g., infrared and visible light images) to identify flora, fauna and/or hydrocarbons. Alternatively, the system may include a UAV and a USV. The UAV may have electromagnetic radiation module (e.g., visible and infrared light cameras) that can be used to investigate larger areas around a USV to detect flora, fauna, hydrocarbons and other marine objects (e.g., ice bergs). Then, the USV may verify that it is desirable to obtain samples in the identified area.

Once the searching stage has identified the target material or verified the area of interest, the sampling stage may be performed in blocks 216 and 226. At block 216, the sample types for an area of interest are determined. The determination of the sample types may include determining whether to acquire water, biological material, chemicals, hydrocarbons and/or other target materials (e.g., types may include obtaining information about aquatic organisms or hydrocarbons). At block 218, one or more samples of target material are obtained. The samples may be obtained by the unmanned vehicle, which may include samples of water, sediment, hydrocarbons and/or other liquids. As may be appreciated, the operation of the unmanned vehicle, which may be automated, may include various processes that repeat during the sampling stage or sample collection operations (e.g., period of time that the unmanned vehicle is obtaining samples). For example, the unmanned vehicle may utilize the one or more measurement components, such as one or more measurement modules, to communicate with the process control unit, to manage the acquisition of the samples, to obtain samples, to calculate operational and sample parameters, to determine adjustments to the operation of the unmanned vehicle and to determine if additional samples should be obtained. Also, the unmanned vehicle may obtain samples, which are associated with aquatic organisms. Exemplary measurement components are described further below. Then, the samples may be stored in or on the UV, as shown in block 220. The storage of the samples may include storing the samples in individual compartments, which are isolated from each other to lessen any cross contamination. The storing of the samples may involve managing the storage temperature of the samples, which may be in the range between about −10° C. and about 10° C., for hydrocarbon samples and between about 10° C. and about −100° C., for biology samples. Exemplary techniques to store of the samples are described further below, which may involve the use of a storage component or module. At block 222, onboard analysis may optionally be performed. The onboard analysis may include analyzing one or more of the samples to verify the target material is present in the sample and/or analyzing one or more of the samples near the time of acquisition of the sample. The onboard analysis may be performed by one or more components on the unmanned vehicle. Then, a determination is made whether the sample collection operations is complete, as shown in block 224. The determination may include obtaining a specific number of samples and/or obtaining certain types of samples. Alternatively, as the samples may include different information, the determination may include analyzing one or more of the samples on the unmanned vehicle via respective modules or components to determine whether additional samples should be obtained. If the sample collection operations are not complete, the unmanned vehicle may move to another potential location, as shown in block 226.

However, if the sampling operations are complete, the further operations stage may be performed, as shown in blocks 228 to 232. At block 228, the unmanned vehicle may be recaptured or redeployed to another potential location of interest. The recapture and redeployment of the unmanned vehicle may include transmitting the location of the deployment vessel for retrieval or having the UV return to a specific location, which may be stored in memory on the unmanned vehicle. Then, at block 230, the obtained samples may optionally be further analyzed. The further analysis of the samples may include providing the samples to a laboratory to perform the analysis, performing the analysis on a marine vessel that deploys the unmanned vehicle, and/or obtaining results from the unmanned vehicle after it performs the analysis and further processing the information. The analysis (which may be performed in a laboratory or onboard a deployment vessel) may include using fluorometry, gas chromatography (GC), mass spectrometry (MS) and/or other suitable GC-MS or GC-GC equipment. Also, the analysis may include DNA sequencing or additional techniques to obtain water chemistry, biodiversity assessments and other characterizations of the environment. In particular, the analysis may include determining the presence of particular species or chemical elements. The samples may be subjected to multiple independent analysis technologies, such as clumped isotope geochemistry, noble gas geochemistry, and microbiology. Each of the analysis may be utilized to provide additional information about the hydrocarbons, biological and/or chemical content of the environment. Then, in block 232, a determination is made whether additional surveying is needed. This determination may involve analyzing the data obtained from the further analysis, data obtained from the onboard analysis and/or operations in the area of interest. The additional surveying may involve biological surveying, chemical surveying and/or hydrocarbon surveying.

As an enhancement to the surveying, the sampling operations may lessen contamination of the samples by removing or inactivating live microbes from some of the obtained samples. The removal of microbes may involve exposing the sample to a compound that kills or inhibits the activity of microbes or degrading enzymes as it is being retrieved or once the sample is within the compartment. For example, the configuration may include a pump and nozzle disposed within each sampling container. Alternatively, sampling material may include a compound that kills or inhibits the activity of living microbes or degrading enzymes captured by the sampling material. Microbes may be inactivated by briefly subjecting the sample to temperature, salinity, or other physico-chemical treatments.

In addition, with the obtained samples, the unmanned vehicle may also obtain other measurement data, such as camera images, temperature data, mass spectrometric data, conductivity data, fluorometric data, and/or polarization data, for example. The data can be in the format of images, raw data with specific format for the component, text files, and/or any combination of the different types. Other sensors may include functionality to provide chemical specificity of applied sensors (e.g., mass spectrometry). The measurements from these sensors may provide guidance on sampling strategy and location.

With the obtained samples and associated data, biodiversity may be modeled based on the analysis of the samples. The analysis of the samples may be integrated with other data to enhance or verify a model. As an example, the sample analysis data may be organized with the location of the unmanned vehicle, and/or another location to correlate the sample analysis data with other measurements or models of the subsurface geology. That is, different types of data may be integrated based on location information associated with the respective data to enhance the characterization operations. For example, sample analysis data may be integrated with photographic images and/or sonic data in a region. Beneficially, the sample analysis data provides an enhancement in the marine surveying of bodies of water. In particular, the method may be utilized prior to drilling operations to establish a baseline for environmental conditions, such as biological and plant diversity as well as for water chemistry, for example. The environmental conditions may be collected over different periods of time (e.g., months, years and other suitable periods of time) and may be integrated with hydrocarbon data (e.g., hydrocarbon models, seismic data and/or other suitable hydrocarbon data) to provide an integrated perspective of the area of interest.

As yet another enhancement, the present techniques may involve the use of two or more unmanned vehicles. For example, one or more sample containers may be transported on a first or deployment unmanned vehicle (e.g., first UAV or USV) to a potential location of target materials in the body of water. The deployment unmanned vehicle may use the identification techniques, noted above, to determine the location of the target materials. Once identified, the deployment unmanned vehicle may drop, lower, launch or otherwise dispose one or more sample containers into the body of water. Once disposed in the body of water, the sampling container may contact the target materials. Then, the sampling container, which may include a sampling material, which has adhered (e.g., sorbed and/or adsorbed) target materials or an acquired fluid and/or sediment sample, is retrieved on a second or retrieval unmanned vehicle (e.g., second UAV or USV). The retrieval unmanned vehicle may be used to store the obtained samples, which may involve the storing of the samples by managing the temperature (with a suitable range for the given samples) within the sample containers on the retrieval unmanned vehicle. The sample containers may be retrieved via a hook and reel configuration, magnet or other suitable retrieval method.

The sample containers may include various configurations. For example, the sample containers may include sample material or sample vessel, as noted above, along with a spool or may include other configurations to obtain samples, such as open tubes that seal at a certain depth or the like. Alternatively, the sample container may be a canister that has the sampling material sealed within the canister's housing. The sample container may include sensor or active component that is utilized to detect the presence of a target material. For example, the sample container may be configured to: maintain the sampling material sealed within the sample container if a particular target material (e.g., hydrocarbon, biological or chemical substance) is not detected; and unseal the sample container to provide interaction between the sampling material and the target material in a body of water when the target material is detected. As another example, the sample container may be configured to: maintain the sampling vessel sealed within the sample container if a particular target material (e.g., hydrocarbon, biological or chemical substance) is not detected; and unseal the sample container to provide interaction between the sampling vessel and the target material in a body of water when the target material is detected. Further, the sealing and unsealing operation may also be configured to be on a timer, remotely activated or any other suitable techniques. In particular, the sample container may be configured to seal the canister after a set period of time once the canister has been unsealed.

To locate the sample containers for retrieval, the sample containers and the retrieval unmanned vehicle may include locating components. That is, the sample containers may include a locating beacon (e.g., an audible notification or other such communication equipment) and the retrieval unmanned vehicle may be configured to detect and navigate to the locating beacon.

To operate, the unmanned vehicle may have a propulsion component, a communication component, a sample component, a storage component, and a measurement component. The propulsion component may be configured to maneuver the unmanned vehicle, the measurement component may be configured to identify target materials, the sample component may be configured to deploy a sample container into the identified target materials, the storage component may be configured to store the sample containers and the communication component may be configured to communicate signals associated with the operation of the unmanned vehicle. To manage the temperature of the samples, the unmanned vehicle may include a storage component (e.g., a heating and/or cooling component) configured to maintain the temperature within the sampling container within a specified range. Further, the measurement component may be configured to provide a mapping of sampling locations, which may be useful for locating survey areas for acquisition of other survey data. For example, if eDNA implies the presence of certain species, other methods may be used to survey the area to determine the number of aquatic organisms in the area.

Figure 3A:
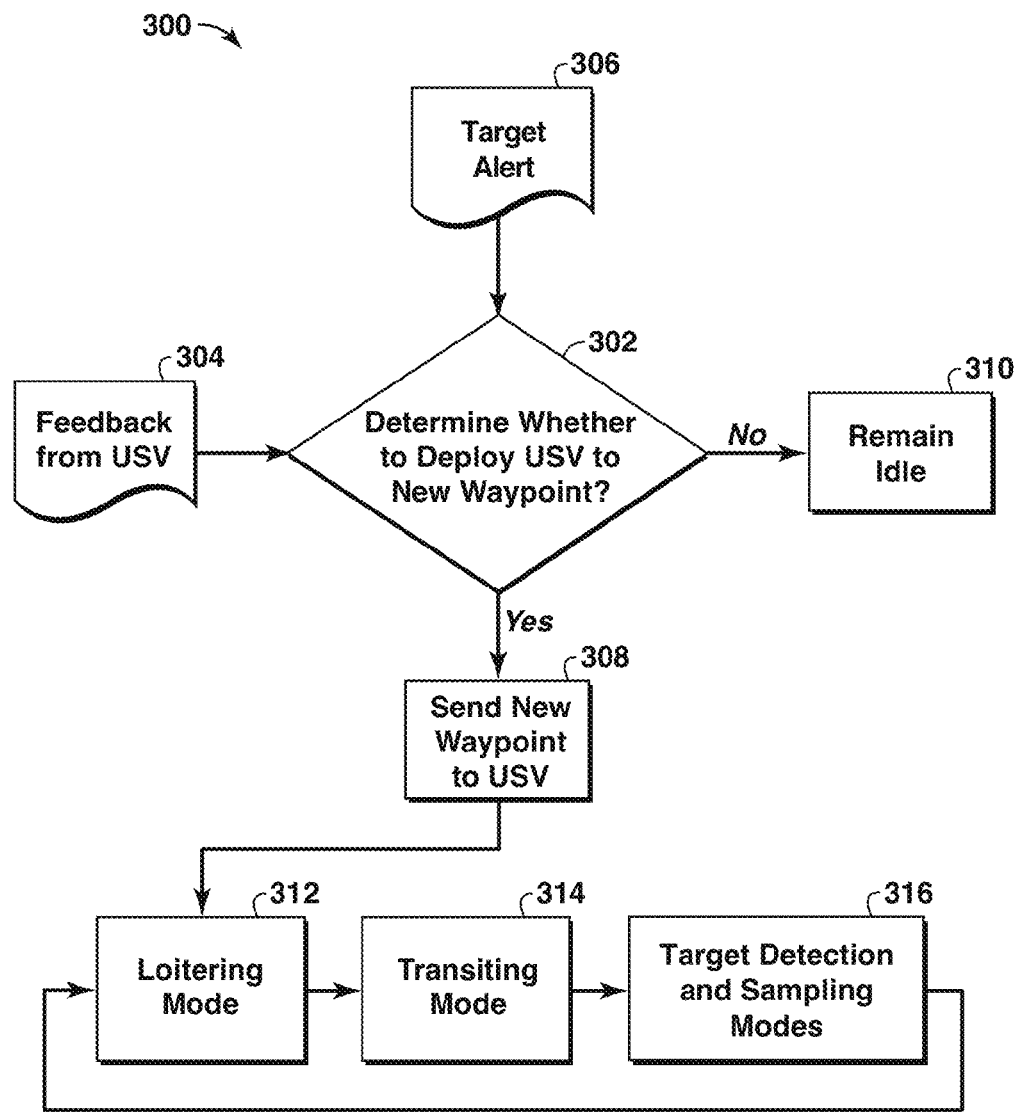
FIGS. 3A and 3B are diagrams for using remote sensing with an unmanned surface vehicle to perform marine surveying in accordance with an exemplary embodiment of the present techniques.

FIG. 3A is a diagram 300 for using remote sensing with an unmanned surface vehicle to perform surveying in accordance with an exemplary embodiment of the present techniques. This example may also be used for a UAV, as well. In this diagram 300, a control unit on the deployment vessel or at a control center may communicate with the unmanned surface vehicle (USV) to perform a marine survey, which may involve target material identification. The control unit functionality is shown in blocks 302 to 310, while the USV's functionality is shown in blocks 312 to 316.

For the control unit on the deployment vessel or at a control center, control logic, as shown in block 302, may be utilized to obtain information from various sources, such as USV feedback data in block 304 and target alert data in block 306; and determine whether to send the USV to another waypoint, as shown in block 308, or maintain the USV in the current mode by remaining idle, as shown in block 310.

For the input data, the target alert data may include satellite images that are acquired and analyzed concurrently with the USV deployment. If target materials of interest are detected, notifications or alerts regarding any potential target materials of interest may be communicated to the control unit or the USV. The location and/or outlines of the target location may be provided in the form of geo-referenced shape files. Then, the location and outlines may be analyzed to determine whether the USV should be deployed to the location. The determination may include analysis of the target materials outline in context with other data and previous target materials indications, and a decision is made on whether or not to target the recently identified target materials. The outlines may indicate a school of fish, waterborne hydrocarbons, or other feature of interest. The USV feedback data may include updates on the location and/or mode of operation for a specific USV.

After a decision is made to target a location of interest, a new or updated waypoint is relayed to the USV, as shown in block 308. The instruction to the USV may include transmitting an updated waypoint, along with a search pattern. The USV may initially be placed into a "loitering mode", as shown in block 312. The "loitering mode" may involve performing energy conservation operations. This may involve the USV remaining idle until another sampling location is provided. For example, the USV may maintain or lessen the components operating in this mode, and operate essential components, such as communications and storage. Once a new location is provided, the USV may enter into a "transiting mode", as shown in block 314. The "transiting mode" may involve the USV traveling to the target material location. The speed that the USV travels may be based on the speed information sent to the USV. In this mode, the USV may maintain the components of the loitering mode along with the components involved in transporting the USV to the location, such as the propulsion component.

Once the USV arrives at the indicated location, the USV enters "target detection mode", as shown in block 316. In "target detection mode", the USV performs a search pattern, which may be communicated to the USV or a stored search pattern. In this mode, additional components may be utilized to detect the target materials and to manage the navigation of the USV. The search pattern may be in a circle, spiral or grid pattern or other appropriate pattern. In "target detection mode", the USV may perform a spiral search pattern, increasing in radius away from the initial waypoint. The hydrocarbon search radius may be around 500 meter (m), with each subsequent radii increasing by about 500 m per rotation. After the USV reaches a radius of perhaps 2 kilometers (km), this pattern is ended or repeated, as appropriate. For example, to detect the waterborne liquid hydrocarbons, the USV may use various sensors to identify the waterborne hydrocarbons. For example, the detection sensors may involve using ultraviolet technology to view the water's surface from some distance above the surface to confirm the presence of waterborne hydrocarbons. See, e.g., Chase et al., 2010. Alternatively, the sensors may include flow-through optical sensors that are used to confirm the presence of hydrocarbons in the water. See, e.g., Dalgleish et al., 2013. As yet another, the USV may have active ultra-violet components that are configured to excite aromatic compounds in hydrocarbons and to detect resulting fluorescence emissions from the surface of the slick. The USV may also have an electromagnetic radiation module (e.g., visible and infrared light cameras) that can be used to investigate larger areas around the USV to locate hydrocarbons, fauna and/or ice bergs, for example.

Once the target materials are verified, then the USV enters into "target sampling mode". In this mode, the USV deploys one of its sampling devices and collects a sample as appropriate for the type of target material to be collected. For example, the USV deploys one of its sampling devices and initiates a new trajectory, such as a sampling pattern. The sampling pattern may have a more narrow radius, as compared to the target search radius (about 10 m radius as compared to 500 m radius) and may be performed at a slower speed (e.g., approximately 1 m/s) spiral. The spiral may increase in radius by about 5 m for every rotation. The spiral may expand to perhaps a 75 m radius before ending. Upon conclusion of this type of sampling operation, the sampling material or sampling vessel is spooled back into the container, and the container is sealed shut. This sealing may isolate the sampling material or sampling vessel from other samples that are obtained to lessen any contamination.

Then, the USV may resume "target detection mode," "target sampling mode" or may enter "loitering mode." As an example, after the USV collects a certain number of samples (e.g., two or more samples) of the target materials, the UV may enter a "loitering mode" until further instructions are provided. This prevents oversampling from a single location.

Figure 3B:
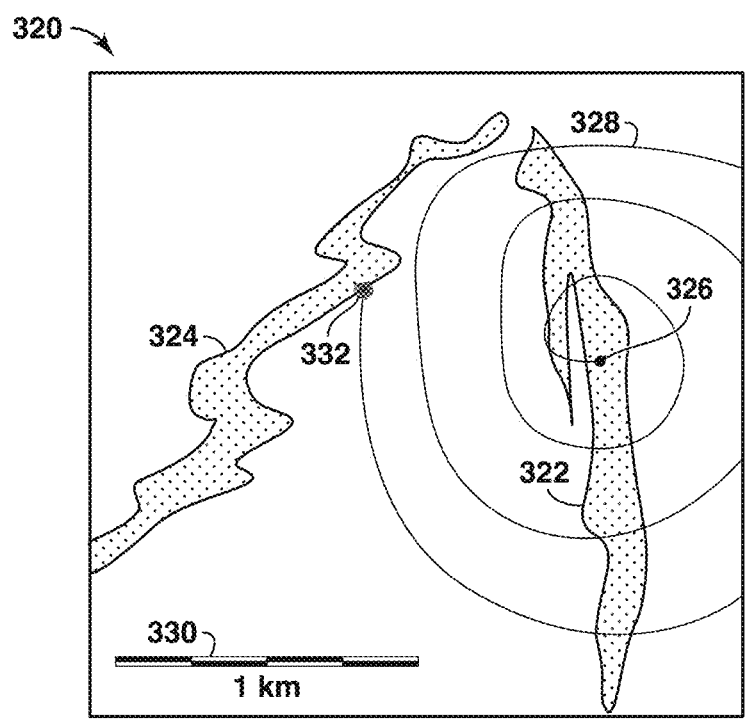

FIG. 3B is a diagram 320 of an exemplary search pattern in accordance with an exemplary embodiment of the present techniques. In this diagram 320, target materials are identified from remote sensing data or a region of interest is identified. Based on environmental conditions, the targeted material may migrate to a different location, as shown by initial target material 322 and the migrated target material 324. Based on the remote sensing data or identified region data, the USV may be directed to an initial waypoint 326 in a "transiting mode". At the initial waypoint 326, if the USV does not detect the target material of interest, the USV may begin "target detection mode" or it may collect data in a grid to identify the location and extent of the target material. That is, the USV may perform a search pattern 328, and then once it detects the target material of interest, as shown at location 332, the USV enters "target sampling mode" or it may go directly into "target sampling mode". While this search pattern is based on the exemplary scale 330, the scale of the search pattern may vary based on various factors, such as the environmental conditions.

To collect samples, the UV (e.g., USV) may include various sampling containers. For example, obtaining of the samples may be performed with the UV having an assembly including 50 to 100 individual sampling containers. Each sample container includes sampling material or sampling vessel that is deployed from the sample container and then retrieved back into the sample container. For the sampling material configuration, the target materials are contacted with the sampling material to adhere to the material, and then the sampling device is retrieved back into the sampling container. The sampling material may be TFE-fluorocarbon polymer screening fabric and may have a thickness of about 0.1 millimeters (mm) to 0.7 mm, or more preferably about 0.3 mm. The sampling container is sealed and temperature-controlled for the duration of the USV deployment. Other sample containers may be lowered to a specific depth, opened, filled, and sealed. These containers may also be kept or maintained in a temperature controlled environment.

Further, as another example, if two or more unmanned vehicle are used, one unmanned vehicle may be used to deploy the sample containers and another unmanned vehicle may be used to retrieve the sample containers. The first unmanned vehicle (e.g., deployment unmanned vehicle) may perform different search patterns. Then, the second unmanned vehicle (e.g., retrieval unmanned vehicle) may either use the search pattern to identify the sample containers or may use the locating techniques to obtain the sample containers. In another example, one vehicle may be used to capture the samples in containers and the second vehicle may be used to store and transport the captured samples. The transport vehicle may take the captured samples back to the deployment vessel or site while the vehicle with the sampling equipment goes into detection mode or loitering mode.

Figure 4A:
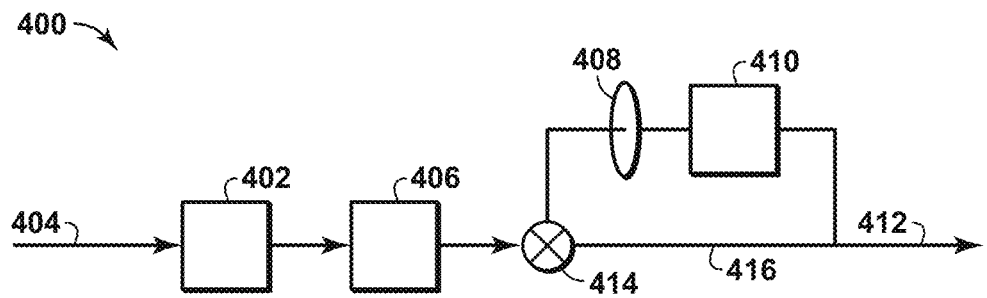
FIGS. 4A to 4E are diagrams for exemplary sampling modules in accordance with an exemplary embodiment of the present techniques.

FIGS. 4A to 4E are diagrams 400, 430, 440, 450 and 460 for exemplary sampling modules in accordance with an exemplary embodiment of the present techniques. In FIG. 4A, a diagram 400 of a detection and sampling module may include a pump 402 coupled to an inlet conduit 404, a target measurement device 406 (e.g., target detection module, such as a fluorometer and/or mass spectrometer), a filter 408, valve 414, a bypass conduit 416 and a solid phase extraction (SPE) module 410, which is coupled to a discharge conduit 412. In this configuration, the pump 402 draws target material (e.g., water and waterborne liquid hydrocarbons) from the body of water. The pump 402 is used to actively move the fluids, which may include liquids, gases and/or solids, from the body of water through the inlet conduit 404 into the target measurement device 406. The fluid is analyzed in the target measurement device 406 to determine if the target material (e.g., hydrocarbons) is present. The fluid is normally directed by the valve 414 to flow directly to the discharge conduit 412 through the bypass conduit 416. If the target measurement device 406 indicates that the fluid contains target material (e.g. waterborne hydrocarbons), then the valve 414 directs at least a portion of the fluid through filter 408, which includes filter media, and the SPE module 410 for a period of time. The SPE module 410 may be a cartridge that is placed into a sample container to isolate the sample from other samples. Solids in the fluid may be adsorbed or captured by the filter media and target material in the fluid may be adsorbed onto the SPE material, while the remaining fluid continues on to the discharge conduit 412. The remaining portion of the fluid at the valve 414 is passed through the bypass conduit 416 to the discharge conduit 412. The portions are combined and passed through the discharge conduit 412. After the sample collection period, the valve 414 is adjusted back to the position that directs the flow of fluids to the discharge conduit 412 through the bypass conduit 416. The used filter and SPE module (e.g., SPE cartridge) may be removed from the bypass conduit 416 and an unused assembly may be inserted to replace the used filter 408 and SPE module 410. Beneficially, this configuration does not involve deployment or retrieval of sampling material. The described module has strong synergies with an unmanned vehicle equipped with a flow-through target detection module (e.g., fluorometer or mass spectrometer) for the purpose of indicating the presence or waterborne liquid hydrocarbons.

Further, in other embodiments, other mechanisms may be used to detect the presence of target material. In such embodiments, the valve 414 may be controlled by signals from the target material detection module. Alternatively, the system may include periodic activation. For example, the valve 414 may be periodically positioned to provide fluid from the body of water to flow through the filter 408 and SPE module 410 to collect one or more samples.

Figure 4B:
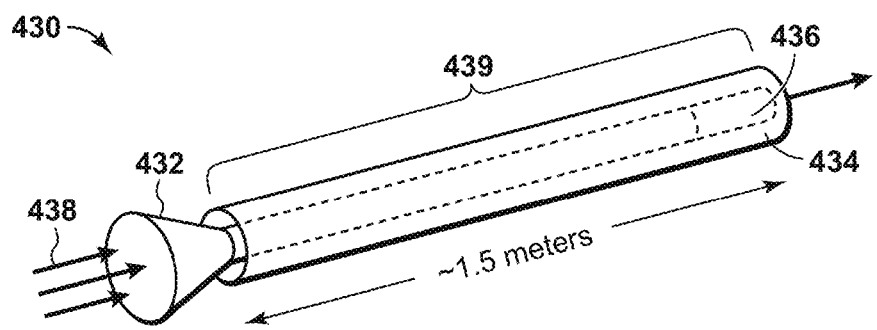

In FIG. 4B, a diagram 430 of sampling module may include a flow diverter 432 coupled to a sampling conduit 434 with a sampling material 436. In this configuration, a fluid is passed through the flow diverter 432 into the sampling conduit 434 to interact with the sampling material. Then, the flow of fluids may be interrupted and the sampling conduit 434, which includes the sampling material 436, may be removed from operations and stored as a sample. The sampling conduit may be sealed at both ends and/or placed into a sampling container for storage to isolate the sample.

Beneficially, this configuration, integrates a larger volume of water to accumulate target materials (e.g., hydrocarbons) to useable levels. The sampling module is a flow-tube accumulator, which may be a passive configuration that can be integrated with other detection systems to unseal the access to the sampling material. Being a passive configuration, the movement of the tide and current may move the fluid through the sampling material, as shown along arrows 438. This configuration lessens power consumption, while providing an enhanced technique for collecting samples. Further, the proposed flow-tube accumulator is configured to extract (e.g., integrate) hydrocarbon droplets as large quantities of fluid are drawn through the sampling conduit 434.

Several configuration considerations may be utilized for this sample module. For example, the platform may be attached to a variety of devices, such as the unmanned vehicles noted above. In a shallow-water environment, the sampling module may be attached to a tow body or otherwise pulled through the body of water. In certain applications, the drag on the sampling module is a lesser concern because the tow body has considerable drag. In deep water applications, the sampling module may be towed behind or incorporated within an underwater vehicle or other submerged vessel. In other applications, power considerations may dictate lessening flow-related drag and may lead to different design choices (e.g., a smaller tube). Another possible platform may involve opening or unsealing the conduits attached to the unmanned vehicle to provide passages for volumes of water to be pulled through the sampling conduit 434 passively and/or using a pump to extract from volumes of water from a specific location.

In another configuration consideration may include different tube structures for the sampling conduit 434 (e.g., funnel; geometric parameters (length, diameter); active versus protected zones). For example, the tube geometry may be adjusted to enhance certain aspects. Parameters to optimize include the tube length 439 and diameter and the possible collecting funnel at the intake. Flow simulation considering these parameters (and the sampling geometry discussed below) may be used to maximize the capture and retention of colloidal hydrocarbon droplets. An optimal flow rate related to these geometric parameters may maximize the capture of droplets over a large filter surface area, while minimizing the stripping out of previously captured sample.

Figure 4C:
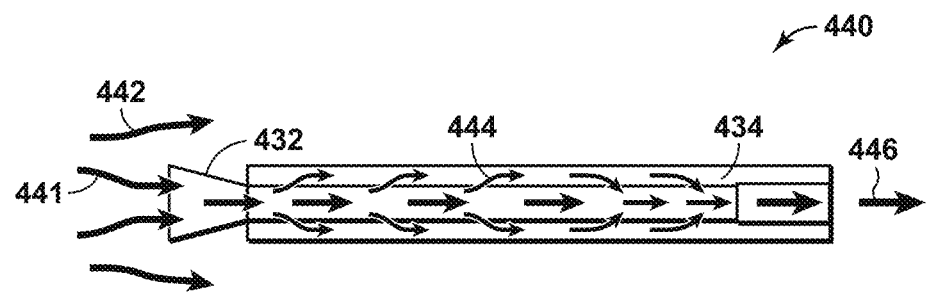

The flow modeling, as shown in FIG. 4C, is a diagram 440 showing the flow of fluids through the sampling conduit 434. Diagram 440 highlights issues like net drag, pressure build up at the intake that diverts flow, parallel paths through the collecting area, and possible turbulent and quiescent regions. In particular, the flow passage represented by arrows 441 enters the sampling conduit 434, while the flow passages represented by arrows 442 bypass the sampling conduit 434. Further, the flow passage as represented by arrows 444 is within the sampling conduit 434, while the flow passages as represented by arrows 446 are exiting the sampling conduit 434.

Figure 4D:
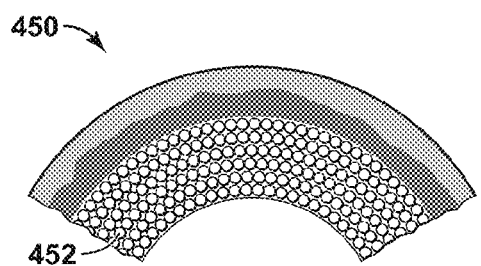
Figure 4E:
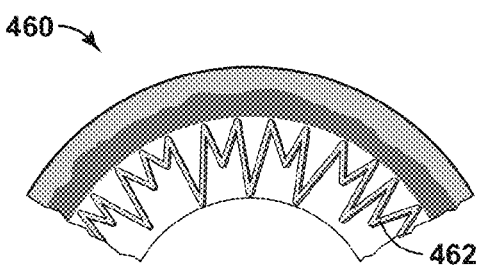

In yet another embodiment, the sampling material may be adjusted for geometry and chemistry. The sampling material geometry may include an annular collecting zone surrounding the central flow channel. A large effective collecting surface with many parallel paths may be desirable to maximize capture with minimal net drag. The sampling geometry may include bead pack; pleated-folded sheet; mesh; sponge; wool; and/or fiber rope. As an example, FIG. 4D is a diagram 450 of a bead pack 452, while FIG. 4E is a diagram of a folded sheet 462. Further, the sampling material chemistry may include a material lining in the sampling conduit (e.g., collecting tube portion) may include one or more materials. These materials may include Teflon sheets or mesh, copper (Cu) or alloys (e.g., bronze wool and/or an antimicrobial), polydimethylsiloxane (PDMS), or silicone paste. Materials may also be coated (e.g., with C18 as in SPE tubes). The sampling material properties may be incorporated into the flow modeling, which may be modeled at different scales to understand local versus large-scale effects.

Figure 5:
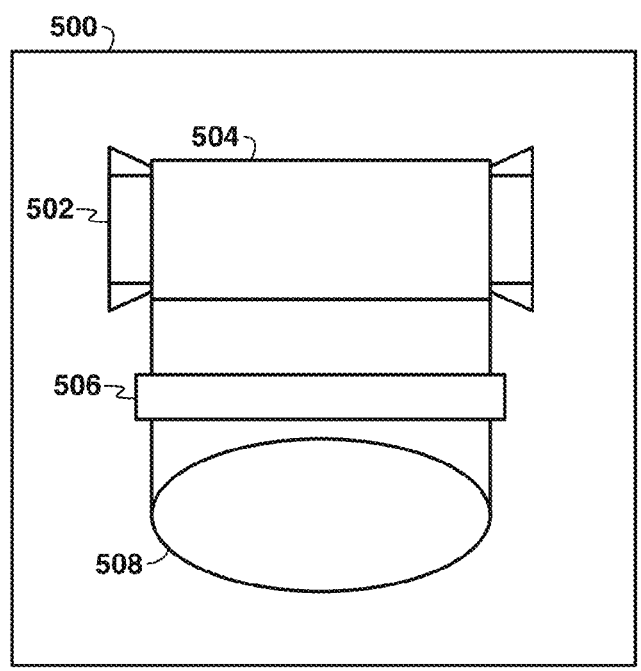
FIG. 5 is a diagram of an exemplary sample container in accordance with an exemplary embodiment of the present techniques.

FIG. 5 is a diagram of an exemplary sample container 500 in accordance with an exemplary embodiment of the present techniques. In this sample container 500, sampling material 504 may be disposed around a spool 502. The sampling material 504 may be attached to the spool 502 at one end, while the other end of the sampling material 504 may be attached to a buoyant weight 508. The buoyant weight 508 may be configured to float on the body of water to maintain the sampling material 504 in contact with the surface of the body of water, may be configured to sink within the body of water to maintain the sampling material 504 at a specific target depth and/or may be configured to contact the sediments at the bottom of the body of water. To control the distribution of sampling material 504, a guide member 506 may be disposed between the spool 502 and the buoyant weight 508. The spool 502 may dispense and retrieve the sampling material 504 through the use of a motor and/or other mechanism (not shown). Beneficially, by having the sampling material 504 in an individual sample container, cross contamination from different samples may be lessened.

As an example, the sampling material 504 may be deployed on a spool 502 that is about 12 centimeters (cm) wide. If the configuration includes 50 to 100 individual sampling containers, each of the individual sampling containers contains one such spool 502. The spool 502 is actuated to activate the deployment and retrieval of the sampling strip of the sampling material 504. The end of the strip is weighted, such as the buoyant weight 508, so that tension exists on the strip to ensure proper deployment down to the desired location (e.g., preventing the strip from being lifted and flapping due to wind) and proper spooling upon retrieval (e.g., slack in the line hinders smooth retrieval). The weight on the end of the strip is buoyant, so that it does not cause the strip to sink below the surface of the body of water or it does not cause the strip to sink below the preferred depth. A metal guide-piece, such as guide member 506, is also in place below the spool to aid in proper spooling and to avoid snagging of the strip on the opening of the sampling container during retrieval. The guide member may have rounded edges to lessen scraping the target material off of the sampling material during retrieval. The guide member may also be configured from two rollers. The guide member also prevents twisting during spooling. The buoyant weight 508 may be configured to not pass through the guide member to provide a stopping mechanism for the spooling mechanism.

The sample container 500 may also include other configurations that may be combined with the sampling material configuration. For example, a sampling vessel, which may replace the sampling material 504, may be coupled to the spool 502 to acquire fluid samples. The sampling vessel may be attached to the spool 502 at one end, while the other end of the sampling vessel may be attached to a buoyant weight 508. Similar to the sampling material configuration, the buoyant weight 508 may be configured to float on the body of water to maintain the sampling vessel in contact with the surface of the body of water, may be configured to sink within the body of water to maintain the sampling material 504 at a specific target depth and/or may be configured to contact the sediments at the bottom of the body of water. Beneficially, the sampling vessel may be placed individually within a sample container to lessen cross contamination from different samples.

In yet another example, an imaging module may replace the sampling material 504 and may be coupled to the spool 502 to acquire images of portions of the body of water. The imaging module may be attached to the spool 502 at one end, while the other end of the imaging module may be attached to a buoyant weight 508. Similar to the sampling material and sampling vessel configuration, the buoyant weight 508 may be configured to float on the body of water to maintain the imaging module in contact with the surface of the body of water and/or may be configured to sink within the body of water to maintain the sampling material 504 at a specific target depth. Beneficially, the imaging module may store images on the UV or may store the imaging module individually within a sample container.

As may be appreciated, the sampling container may involve different configurations. For example, the sampling container may be a rectangular prism to maximize the packing density of the containers and thus the quantity of samples onboard for a given space. These sampling containers may include various different types of target materials in the individual sampling containers. The bottom surface may be a swinging door that is opened and closed using an electric motor that is housed outside of the sample container. Actuators may be disposed outside of the sample container to avoid contamination issues caused by lubricant oil, etc. The door may swing open using a hinge at one end of the sample container, such that the sample material may exit the sample container using gravity. The door orientation may be configured to prevent the door from interfering with the sample material as it is deployed and retrieved (e.g., positioned at the end of the sampling container that is near the front of the UV. When the door is opened, it should open as wide as possible, so as to avoid contacting or interfering with the sample material, sampling vessel or other sampling module. The hinge should be configured to lessen it as a source of sample contamination, so the materials and lubrication should be carefully considered here. The door should make a tight seal when it is closed to isolate the sample material, sample vessel or other sampling module and oil sample from the environment. The doors may be firmly sealed even in extreme sea states where they are being rapidly accelerated and decelerated and being struck by waves. The seal may preferably be air and water tight. The door may also include a thermally insulating layer to reduce heat loss to the environment. The motor should be IP66 certified, which certifies that the device is dust tight and can prevent water ingress even while being washed down under high pressure. The rugged operating environment makes this necessary. The door and motor drive described are shown in FIGS. 6 and 7.

Figure 6:
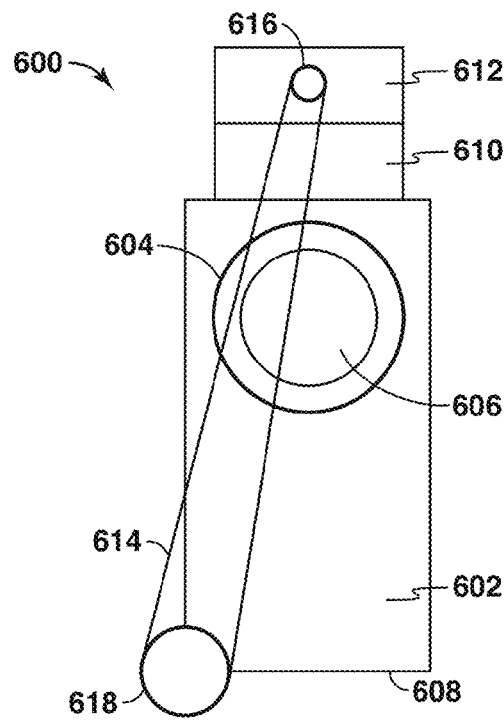
FIG. 6 is a diagram of an exemplary sample container having a motor drive in accordance with an exemplary embodiment of the present techniques.

FIG. 6 is a diagram of an exemplary sample container configuration 600 having a motor drive for the door in accordance with an exemplary embodiment of the present techniques. In this configuration 600, the sample container 602 may include a sampling material 604 may be disposed around a spool 606. Similar to the discussion of FIG. 5, the sampling material 604 may be attached to the spool 606 and use buoyant weight and guide member (not shown). In this configuration 600, a door 608 is disposed at the end of the sampling container adjacent to the body of water. The configuration 600 includes a first electric motor 610 that may be used to operate the spool 606 and a second electric motor 612 that is utilized to open and close the door 608. The first electric motor 610 is utilized to operate the spool 606 to deploy and retrieve the sampling material 604. The second electric motor 612 is utilized to open and close the door 608, which may utilize a belt or chain 614 and pulleys 616 and 618. As may be appreciated, other configurations may include a sample vessel or other sampling module instead of the sampling material.

Figure 7:
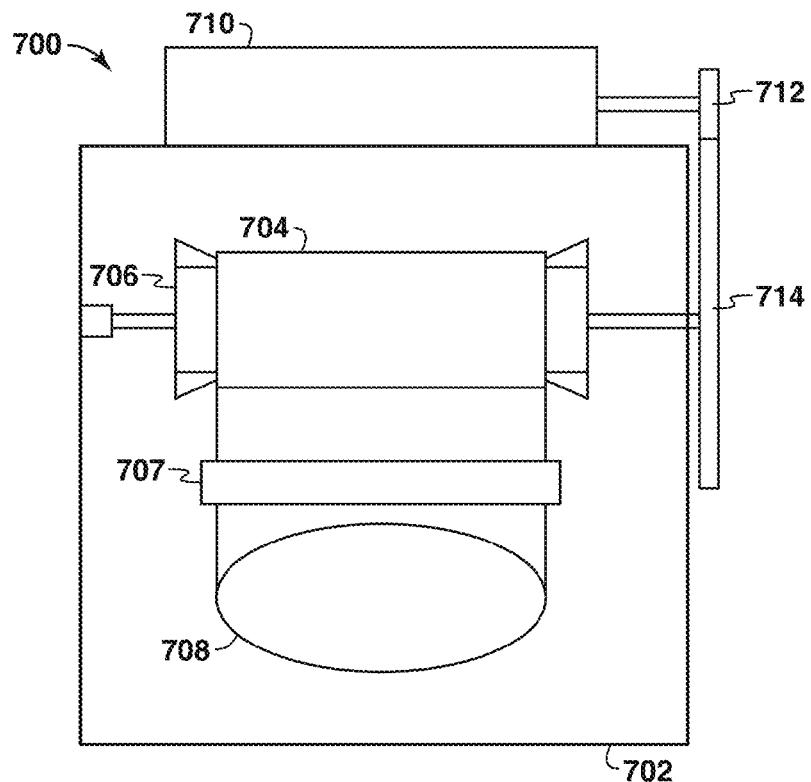
FIG. 7 is a diagram of an exemplary sample container configuration having a motor drive for the spool in accordance with an exemplary embodiment of the present techniques.

FIG. 7 is a diagram of an exemplary sample container configuration 700 having a motor drive 710 or the spool 706 in accordance with an exemplary embodiment of the present techniques. In this configuration 700, the sample container 702 may include a sampling material 704 may be disposed around a spool 706. Similar to the discussion of FIGS. 5 and 6, the sampling material 704 may be attached to the spool 706 and use buoyant weight 708 and guide member 707. The electric motor 710 may be used to deploy and retrieve the sampling material 704 from the spool 706. The electric motor 710 is configured to engage with a shaft and a first gear 712, which is configured to engage with the second gear 714. The second gear 714 may be configured to engage with a shaft that coupled to the spool 706.

Through this coupling, the electric motor 710 deploys and retrieves the sampling material 704. The spool 706 may be rotated by the electric motor 710 to deploy and retrieve the sampling strip of sampling material 704. The actuator may be placed outside of the container to avoid contamination, and may be placed on top of the sampling container 702 to reduce the footprint of the sample container 702. The rotational motion may be transmitted to the spool axle via gears 712 and 714 on the outside of the sample container 702. The electric motor 710 and gears 712 and 714 may or may not need to have additional housing around them. The other end of the spool axle may be seated in a bearing hole to provide free rotation, while holding the axle in place. The motor 710 may be dust tight and can prevent water ingress even while being washed down under high pressure (e.g., IP66 certified). In this configuration 700, the sample container's opening through which the spool axle extends may also be sealed. That is, it should be an airtight and watertight seal to avoid any contamination. Additionally, the sealing material 704 may be considered as it could be a source of sample contamination. While it may be preferred to not use any lubrication for the spool axle (as shown in FIG. 7), it should be configured to lessen any sample contamination from the lubrication. As may be appreciated, other configurations may include a sample vessel or other sampling module instead of the sampling material.

To enhance the operations, the spool may be configured to easily install and remove from the sample container. That is, the sample containers may be configured to provide easy removal and insertion for shipment to the lab. Accordingly, the configuration may include a design that provides a spool gear that is easy to remove (e.g., with a pin or nut securing the gear into the system). After the gear is removed, then the spool axle may be pulled out of the sample container, which results in the spool being free to drop out of the sampling container. A new spool may then installed by placing it into the container, sliding the axle, which may be keyed, through the spool, and securing the gear back on to lock the spool in place. As an example, the sampling container may be approximately 16 cm in width, 4 cm in depth, and 11 cm in height with an additional 5 cm of height below the container to accommodate the swinging door.

Figure 8:
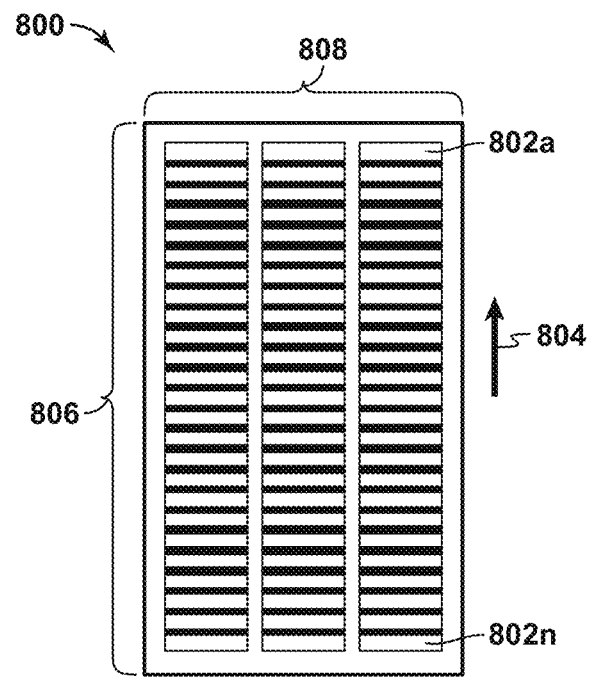
FIG. 8 is a diagram of an exemplary sample assembly having multiple sample containers in accordance with an exemplary embodiment of the present techniques.

The sample containers may be arranged into different configurations and may include different types of samples. For example, the sampling containers may be arranged and mounted within the sampling assembly, as shown below in FIG. 8. FIG. 8 is a diagram of an exemplary sample assembly 800 having multiple sample containers 802*a* to 802*n* in accordance with an exemplary embodiment of the present techniques. In this configuration 800, the sample assembly may be a rectangular prism that includes from 50 to 100 sampling containers 802*a* to 802*n*, which are also rectangular prisms. The sampling assembly may have a height 806, a width 808 and depth (not shown), which provide the dimensions of the rectangular prism. As an example, the sampling assembly 800 may be approximately 0.6 meters (m) in width, 11 cm in depth, and 1 m in height. This sampling assembly of such dimensions may include 75 sampling devices. The diagram is a view of the doors for the sampling containers 802*a* to 802*n*, which may have one or more electric motors to open and close the doors and deploy and retrieve the sampling material from within the individual sampling containers 802*a* to 802*n*. The sampling assembly may include additional space above for the motor and other components (e.g., which may be housed inside an enclosure) and have an additional space of about 5 cm of height below the container to accommodate the swinging door for the sampling containers 802*a* to 802*n*.

The actual size of the sampling assembly depends largely upon the UV platform. In the sampling assembly, a gap around each sampling container (e.g., between 2 cm to 4 cm or about 3 cm) except where the containers are adjacent and connected to each other in the fore-aft direction. The fore and aft walls of the sample containers may be a shared piece of metal plate. The 3 cm gap may be utilized to accommodate the gear and belt drives on either side of the sampling containers and also to provide mechanism to flow a cooling fluid between the sampling containers. The temperature control components are explained further below.

In other configurations, the different types of samples may be stored in different portions of the UV. For example, hydrocarbon samples may be stored in a first portion that is managed at a first temperature, while biological samples are stored in a second portion that is managed at a second temperature. Further, the chemical samples may be stored with the hydrocarbon samples or may be stored in a third portion that is managed at a third temperature.

Figure 9:
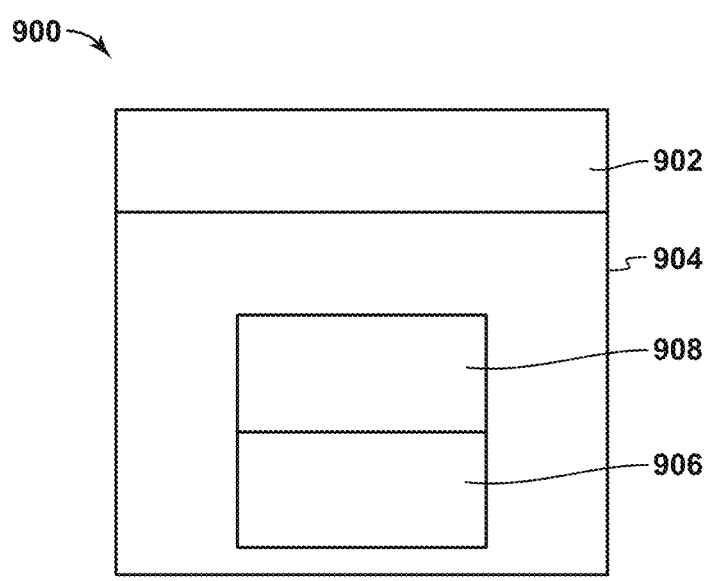
FIG. 9 is a diagram of an exemplary unmanned vehicle in accordance with an exemplary embodiment of the present techniques.

To collect samples, the sampling assembly may be disposed on an unmanned vehicle, as shown in FIG. 9. FIG. 9 is a diagram of an exemplary unmanned vehicle 900 in accordance with an exemplary embodiment of the present techniques. In this diagram, the sampling assembly 906 is disposed on an unmanned vehicle 904, which includes various components 902, which may be utilized for communication, sampling, detection and/or identification, power distribution and/or propulsion along with managing autonomous operations, if necessary. The sampling assembly 906 may include various individual sample containers that are used to obtain samples (e.g., deploy the sampling material onto the surface of the body of water). For example, the sampling material, which may be a strip, is sized so that approximately 1 m of the sampling material is in contact with the water's surface during sampling. The strip is then dragged through the target materials based on the sampling pattern before being retrieved back into the sampling container, which is subsequently sealed shut. For other configurations, the sampling material is sized so that approximately 1 m of the sampling material is in contact with the body of water at the desired depth during sampling.

Further still, the materials of construction of the UV and sampling assembly are evaluated to consider any possible contamination effects they may have on the obtained samples. Adequate freeboard may be preferred, so that the sampling material is not lifted by waves into the bottom surface of the sampling assembly during sampling operations. The configuration of the UV may be such that sampling may occur without the sampling material coming in contact with any part of the vessel.

Further, the unmanned vehicle 900 may also include heating and cooling or storage component 908 configured to maintain the temperature of the samples within a specified range (e.g., between about 10° C. and about −100° C.). For example, the sample temperatures for hydrocarbon samples should be maintained above −10° C. (e.g., for hydrocarbons this prevents irreversible crystallization of waxes). Samples for microbial ecology may be preserved at temperatures lower than −10° C., such as in a Dewar of liquid nitrogen. As an example, the temperatures for biological samples may be between about −10° C. and about −100° C. or between about −20° C. and about −100° C. Further, if the sample temperatures are too high, bacteria may degrade the sample. Accordingly, storage component 908 may maintain the samples at temperatures between about −100° C. and 10° C., temperatures between about −5° C. and 10° C., and/or temperatures between about 4° C. and 5° C., which may be specified in ASTM D4489-95.

The cooling and heating or storage components 908 may include various modules to operate. For example, the storage components 908 may include a mobile temperature management unit that maintains a heat transfer fluid. Exemplary mobile temperature management units are commercially available and utilized for the transport and temperature control of biological samples. In this configuration, the heat transfer fluid should be configured to not freeze or vaporize in expected temperatures that the UV may be exposed to during operations. The heat transfer fluid should also be compatible with the materials with which it is in contact. The temperature of the heat transfer fluid is controlled inside of the mobile temperature management unit, and it is circulated inside of the sampling assembly to heat or cool the sample containers, keeping their temperatures in the acceptable range.

Figure 10:
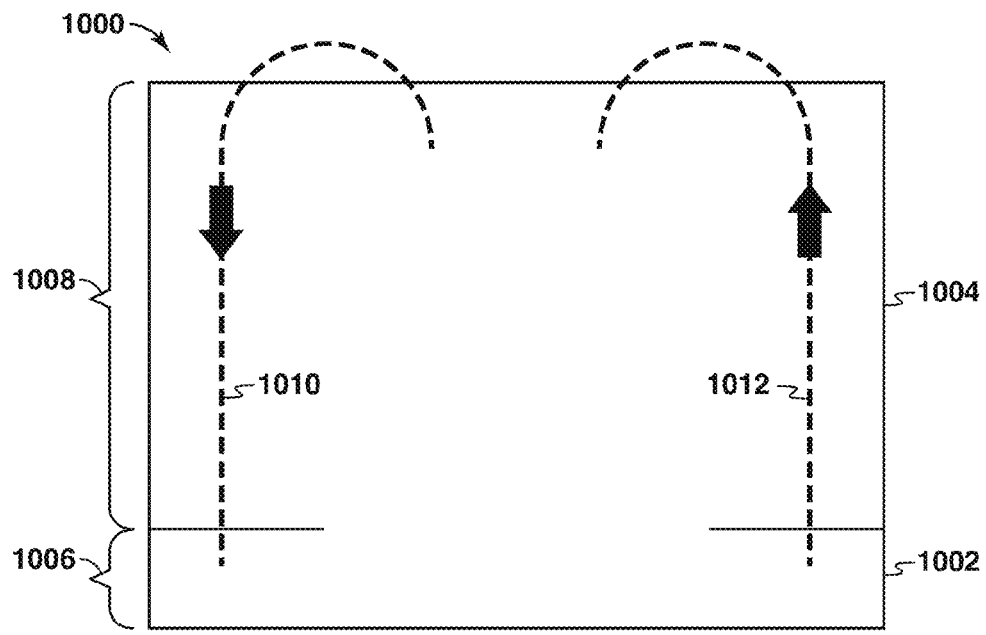
FIG. 10 is a diagram of an exemplary sample assembly and storage component in accordance with an exemplary embodiment of the present techniques.

As an example, FIG. 10 is a diagram 1000 of an exemplary sample assembly 1002 and storage component 1004 in accordance with an exemplary embodiment of the present techniques. In this diagram 1000, the sampling assembly 1002 is disposed below (e.g., closer to the body of water than) the storage component 1004. The storage component 1004 may include various conduits, temperature control sensors, heat transfer fluid and pumps that are utilized to maintain the sample containers within the sample assembly 1002 within a predetermined temperature range. As an example, the sampling assembly 1002 may have a depth 1006 of 0.15 m, while the storage component 1004 may have a depth 1008 of 0.6 m. The length and width may vary, but may be similar to the sampling assembly. As noted above for the sampling assembly example, the storage component 1004 may have a length that is 1 m and the width is 0.6 m, which may be disposed over the sampling assembly.

To maintain the temperature, the heat transfer fluid may be circulated, as shown by arrows 1010 and 1012, using a small pump located inside of the storage component 1004 or elsewhere. For cold environments, the heat transfer fluid may be a water-based fluid combined with an anti-freeze agent to prevent ice from forming. For warmer environments, the heat transfer fluid may include water and/or seawater. Other fluids and additives are also considered and combined with the heat transfer fluid, as may be appreciated. The heat transfer fluid does not have to completely fill the areas of the sampling assembly outside of the individual sampling containers. That is, an air gap may be provided in the top portion of the sampling assembly, so that any electric motors are not submerged. Further, the sampling assembly may be compartmentalized to contain the heat transfer fluid below a certain level to reduce the amount of contact with the electric motors.

To manage the temperature, one or more thermocouples may be disposed in each sample container or adjacent to the sample containers to monitor the sample temperatures. This information may be stored (e.g., logged) and/or communicated to a control unit that may adjust the temperature by changing setting in the storage component 1004.

To provide quality assurance, a camera may be utilized to capture different aspects about the operations. That is, the camera may record interesting time segments of sampling operations in video or snapshot form and/or may be used to obtain images associated with aquatic organisms. The camera may specifically record the deployment and/or sampling operations for each sample. Further, the camera may be utilized to capture biological data, as well.

In one or more configurations, the samples may be processed on the UV via measurement components. Alternatively, the samples may be transported to another location for analysis. The analyses may include chemical and isotopic analysis (e.g. mass spectrometry and/or fluorometry and/or analysis for noble gases and isotopologues), sediment analysis, biological analysis (e.g., DNA analysis), and/or other methods. See, e.g., Chase, C. R., Lyra, G., & Green, M. (2010, October). Real-Time Monitoring of Oil Using Ultraviolet Filter Fluorometry. Sea Technology.

In one or more embodiments, the UV may be an unmanned surface vehicle and/or an unmanned airborne vehicle. If the UV is an unmanned surface vehicle, it may be a catamaran-style USV that is less than seven meters long and travels at speeds less than seven knots (kn). The USV may be transported in a standard twenty foot container from a deployment vessel. It may be deployed from a variety of vessels of opportunity or from the shore locations. A transit speed of around three and a half knots is sufficient, while faster travel may be preferred to reduce the time between satellite acquisition and reaching a sampling location.

The UV may be configured to perform the search and sampling patterns described in the previous paragraphs in an automated manner and/or via remote operations. For example, the UV may be deployed from a vessel performing other operations (e.g., seismic survey). Then, the UV may be launched into the body of water when target materials are identified or a region of interest is identified. The operations of the UV may be controlled from the vessel by an operator. After deployment, the UV is controlled from the vessel from which it was launched or from another shore-based location. The UV is then retrieved from the body of water by the same vessel from which it was deployed or from shore or another vessel.

Data from the sensors onboard the UV may be communicated back to operators via communication equipment (e.g., Iridium satellite) and stored and analyzed in a database, while the UV is deployed. Commands may be sent to the UV from the shore or from a manned vessel. While the communications may be based on a variety of technologies, the UV may use an Iridium satellite link to provide the primary means for communicating navigation and sensor measurements to the remote operator. The same system may also be used as the primary means of relaying commands to the vehicle. When higher bandwidth is required, perhaps during sampling activities, the RUDICS satellite communication system may be used, for example.

In additional embodiments, the sensors include a UV-fluorometer(s) to screen the screen potential target materials for possible anthropogenic contamination (e.g., diesel fuel) or other substances that indicate that the target materials are not sample contamination. Additionally, these sensors within an UV can be used to map chemical or physical anomalies around target materials to locate the potential discharge locations. The analysis of the target materials may provide information based on biological and chemical sampling of fluids, gases, and sediments.

In one or more embodiments, the unmanned vehicle may include other components to perform the operations. For example, the UV may include a housing that encloses one or more of a communication component and associated antenna, a sample component, another measurement component, a power component and a propulsion component on one or multiple UVs. The modules and components may be provided power from the power component via power distribution lines. Similarly, the different modules and components may communicate with each other via communication lines. The central power and communication lines may be enclosed to be isolated from the environment and to manage the operation in an efficient manner.

To operate, the power component may be utilized to supply power to the propulsion component. Further, the power component may provide power to the communication component and the other measurement components and temperature regulation components. The power component may include a battery, motor and/or solar powered equipment. The batteries may provide power via the power distribution lines, which may include one or more cables, as an example. The motor may turn fuel into power through a generator, which may be used to power the modules and components and also to recharge the batteries.

The communication component may be utilized to exchange information between the different modules and components and/or the command unit via the communication lines and the communication antenna. The communication component may utilize the communication lines to handle the exchange of information, such as measured data, status indications or other notifications between the modules, such as the sample component, the other measurement components, the power component and the propulsion component. The communication lines may include a bus, Ethernet cable, fiber optics or other suitable physical connection. In an alternative embodiment, the communication between modules may be via a wireless connection. Similarly, the communication protocol may be any protocol known to those skilled in the art. The communication components may include communication equipment that is utilized to communicate with one or more of other unmanned vehicles, marine vessels and/or command units. The communication equipment may utilize technologies, such as radio, cellular, wireless, microwave or satellite communication hardware and software.

To sample and measure the target materials, the sample component may be utilized to measure various features of the target materials. Examples of different measurement components and the associated techniques to obtain measurements are noted further above.

Further, in one or more embodiments, the present techniques may include a method of marine surveying that includes utilizing distributed sensor network to identify locations of particular target materials. The sensors in the network may include nanoparticles, quantum dots, composites, films, filters, molecular sieves, and/or other analytical devices method. The distributed sensor network may communicate by producing a signal (e.g., auditory, visual, and/or infrared) that is measurable or may be detected by a detector. The detectors may include remote sensing components that are tuned to the signal (e.g., signal frequency produced by the signal generators). The distributed sensor network may also utilize signal relays or other mechanisms to communicate between different components (e.g., individual sensors, sensor platforms and/or a control unit) and maintain connectivity during the survey period. In particular, it may be advantageous for the sensor networks to be nested, in that different decision criteria or algorithms may be used to resolve the location and potential source of an identified target. For example, with seepage from a vessel, it may be advantageous to select a more general compound that is unique or above compounds that are typically observed in the background environment, but may not be diagnostic for the target of interest. The distributed sensors may survey, perhaps using a simple algorithm (e.g., binary or "yes/no" indications), to determine whether the target material (e.g., compound of interest) exceeds a pre-selected threshold. Once the initial survey area has been determined, additional surveying and evaluation may continue until the area containing the target material has narrowed markedly. These distributed sensors may then signal a control unit or other device to indicate the presence of a target material. Then, the AUV may be deployed to conduct detailed surveying and sample collection within the area defined by the sensor network (e.g., identified location). Beneficially, the use of the sensor network may lessen the survey area to provide a lower-cost method that utilizes low-power devices in addition to and/or prior to deploying an AUVs and/or other sampling platforms.

In yet other embodiments, the present techniques may be utilized to further provide treatments to an area of interest. For example, if hydrocarbons are detected, the identity of the source of the hydrocarbons may be a seep or equipment. If the source is equipment, a treatment program may be initiated using the data obtained by the present techniques. As a specific example, if an UV detects a plume, the source may be identified and treatments (e.g., dispersants) may be delivered to the identified location. Accordingly, probes may be used to narrow the search area, then one or more UVs may obtain samples at the target location. Further, as the UV may refine characterization of the samples, additional probes may be used to provide treatments to the source. Also, the probes may implement a contamination strategy (e.g., to release some of a containment material or fluid). The probes may be used to monitor the extent the contaminant spreads from the source. For example, if the probes are configured to track concentrations of a particular component in the chemical above a particular threshold, then the probes may provide an opportunity to maintain the extent of the spread or dispersal of the plume may be monitored as the probes follow the plume. Preferably, the probes may be configured to have different thresholds based on the concentrations above a first threshold and then with concentrations above a second threshold or a threshold for a different compound. In addition, the probes may be configured or tuned to monitor between two thresholds for a particular compound to map the edge of a plume.

In yet other embodiments, the present techniques provide an enhanced marine surveying method that obtains information for biodiversity at different trophic levels, such as using environmental deoxyribonucleic acid (eDNA) (e.g., environmental surveying). The present techniques may provide useful information on the impact of an event or ongoing anthropomorphic features, for water borne pathogens, both biological, hydrocarbon and chemical, and for studying invasive or endangered species. As one embodiment, a sensor array may provide an enhanced signal indicating the presence of a particular chemical, hydrocarbon and/or biological target, which may be utilized to enhance the efficacy of surveying and sampling operations. This enhanced signal may be produced by a signal generator on a sensor array or network that amplifies natural geochemical signals (e.g., fluorescence) or creates additional signatures that complement or augment data typically used by traditional surveying techniques (e.g., spectral character of feature may be amplified or augmented by signals generated with different wavelength). The sensor array may include various probes, which may generate signals when a chemical exceeds a particular threshold and may enhance identification and detection, particularly when used in addition to ship-based or remote sensing techniques (e.g., airborne and/or satellite). Enhancing target identification, location, and providing real-time geochemical information may be particularly useful for rapid or timely responses to the environmental surveying operations. The distributed sensor arrays may utilize low amounts of power and may provide a relatively inexpensive means to identify the boundaries or distribution of a particular target material. By coupling distributed sensor arrays with one or more UVs or similar technologies, one or more of the UVs can be deployed in a more targeted area, with sampling optimized based on a grid pattern or boundaries indicated by the sensor arrays. As such, the use of higher-end, more expensive sample acquisition can be reserved to focused target areas. Samples acquired from targeted locations or sampling intervals can then be used to construct detailed biological, hydrocarbon and/or chemical surveys for the area of interest (e.g., target area). These techniques may efficiently obtain samples from locations in bodies of water in a more accurate, efficient and cost-effective manner.

The UV may include other features as well. For example, the UV may include an obstacle avoidance system to avoid other vessels, ice, and other hazards.

Figure 11:
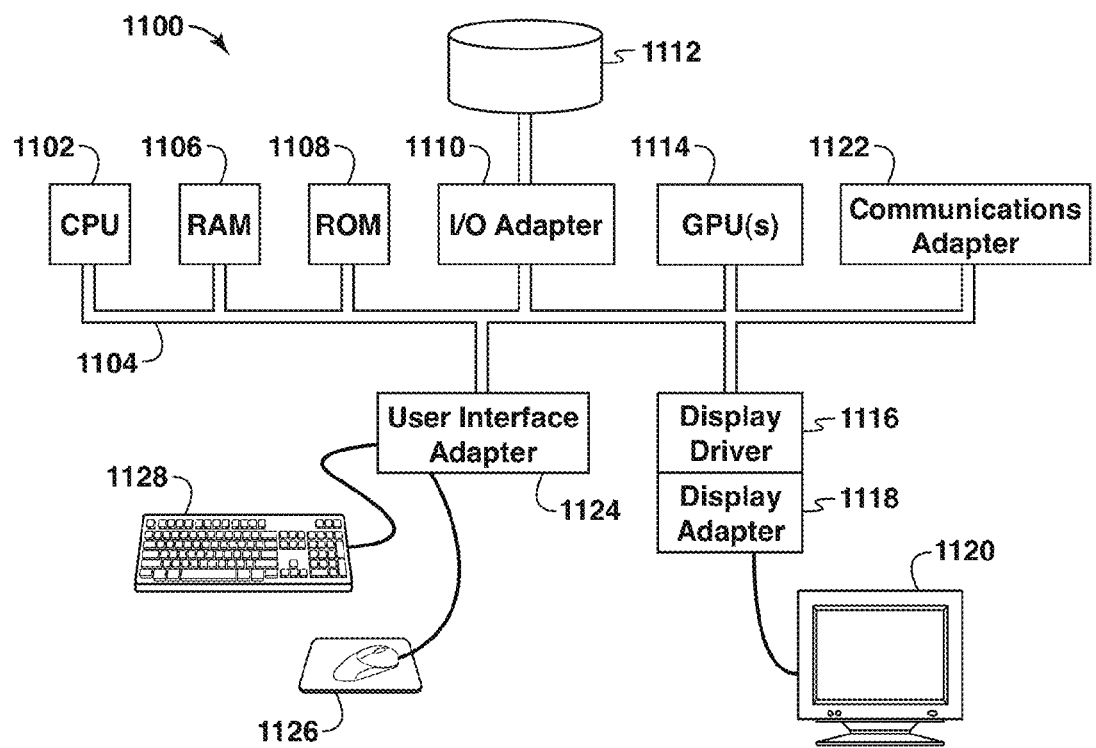
FIG. 11 is a block diagram of a computer system that may be used to perform any of the methods disclosed herein.

As an example, FIG. 11 is a block diagram of a computer system 1100 that may be used to perform any of the methods disclosed herein. A central processing unit (CPU) 1102 is coupled to system bus 1104. The CPU 1102 may be any general-purpose CPU, although other types of architectures of CPU 1102 (or other components of exemplary system 1100) may be used as long as CPU 1102 (and other components of system 1100) supports the inventive operations as described herein. The CPU 1102 may execute the various logical instructions according to disclosed aspects and methodologies. For example, the CPU 1102 may execute machine-level instructions for performing processing according to aspects and methodologies disclosed herein.

The computer system 1100 may also include computer components such as a random access memory (RAM) 1106, which may be SRAM, DRAM, SDRAM, or the like. The computer system 1100 may also include read-only memory (ROM) 1108, which may be PROM, EPROM, EEPROM, or the like. RAM 1106 and ROM 1108 hold user and system data and programs, as is known in the art. The computer system 1100 may also include an input/output (I/O) adapter 1110, a communications adapter 1122, a user interface adapter 1124, and a display adapter 1118. The I/O adapter 1110, the user interface adapter 1124, and/or communications adapter 1122 may, in certain aspects and techniques, enable a user to interact with computer system 1100 to input information.

The I/O adapter 1110 preferably connects a storage device(s) 1112, such as one or more of hard drive, compact disc (CD) drive, floppy disk drive, tape drive, etc. to computer system 1100. The storage device(s) may be used when RAM 1106 is insufficient for the memory requirements associated with storing data for operations of embodiments of the present techniques. The data storage of the computer system 1100 may be used for storing information and/or other data used or generated as disclosed herein. The communications adapter 1122 may couple the computer system 1100 to a network (not shown), which may enable information to be input to and/or output from system 1100 via the network (for example, a wide-area network, a local-area network, a wireless network, any combination of the foregoing). User interface adapter 1124 couples user input devices, such as a keyboard 1128, a pointing device 1126, and the like, to computer system 1100. The display adapter 1118 is driven by the CPU 1102 to control, through a display driver 1116, the display on a display device 1120. Information and/or representations of one or more 2D canvases and one or more 3D windows may be displayed, according to disclosed aspects and methodologies.

The architecture of system 1100 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

In one or more embodiments, the method may be implemented in machine-readable logic, such that a set of instructions or code that, when executed, performs automated sampling operations from memory. That is, the UV may be configured to operate in an autonomous mode. As an example, operating in an autonomous manner may include navigating and sampling the potential target materials without the interaction of an operator. In such configurations, the UV may include a control unit, which may be the computer system 1100 as noted in FIG. 11. During the deployment, the unmanned vehicle may navigate toward targeted locations or may navigate along a specific search pattern. To navigate, the unmanned vehicle may utilize navigation components, which may include one or more propulsion components, one or more steering components and the like. The one or more propulsion components may include a motor coupled to one or more batteries and coupled to a propeller assembly, via a shaft, for example, as is known in the art. The propeller assembly may be utilized to move fluid in a manner to move the unmanned vehicle relative to the body of water. The navigation components may utilize sensors or other monitoring devices to obtain navigation data. The navigation data may include different types of navigational information, such as inertial motion unit (IMU), global positioning system information, compass information, depth sensor information, obstacle detection information, SONAR information, propeller speed information, seafloor map information, and/or other information associated with the navigation of the unmanned vehicle. The deployment may also include inserting certain equipment (e.g., certain monitoring components) into the unmanned vehicle for use in sampling operations. As an example, the deployment may include lowering the unmanned vehicle from the deck of a marine vessel into the body of water or dropping the unmanned vehicle into the body of water from an airborne vehicle.

The control unit may manage the operations of the communication components, sampling, detection and identification components, power components and propulsion components. The control unit may be configured to direct the navigation components to follow a direct trajectory to a target location and/or follow one or more search patterns. This may also involve adjusting operational parameters and/or settings to control the speed and direction. Further, the control unit may adjust the operation of the detection and identification components. That is, the control unit may have the detection and identification components perform the detection operations in a specific sequence. For example, the operations may involve deploying the unmanned aerial vehicle (e.g., a balloon) or a UAV with detection equipment to identify locations. Then, the fluorometer and/or wavelength detection components may be utilized. This configuration may conserve power by having the long range detection components utilized initially, while the other short range components are utilized to verify the target material location.

Further, the control unit may also control the sampling operations. As noted above, the sampling operations may be controlled by the control unit to obtain a certain number of samples, the duration the samples are in contact with the target material and other such operational aspects. It should be understood that the preceding is merely a detailed description of specific embodiments of the invention and that numerous changes, modifications, and alternatives to the disclosed embodiments can be made in accordance with the disclosure here without departing from the scope of the invention.

The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other.

The invention claimed is:

1. A method for performing a marine survey comprising:
    a) transporting a plurality of sample containers on an unmanned vehicle to a potential location of target material in a body of water, wherein the target material comprises one or more of biological, chemical, hydrocarbons, and any combination thereof and wherein the unmanned vehicle is one of unmanned surface vehicle and an unmanned airborne vehicle;
    b) detecting the presence of the target material in the body of water and if the target material is present in the body of water obtaining a sample of the target material;
    c) disposing the obtained sample into one of the plurality of sample containers on the unmanned vehicle; and
    d) repeating the steps (b) to (c) for another sample, wherein the obtained samples are stored in individual sample containers of the plurality of sample containers.

2. The method of claim 1, further comprising performing remote sensing in a survey area to identify the potential location of the target material.

3. The method of claim 1, further comprising inhibiting microbial or enzymatic activity from the obtained sample.

4. The method of claim 1, wherein obtaining the sample of the target material comprises:
    contacting sampling material from one of the plurality of sample containers with the target material; and
    retrieving the sampling material having adhered target material as the obtained sample into one of the plurality of sample containers.

5. The method of claim 1, wherein obtaining the sample of the target material comprises:
    unsealing a sampling vessel to obtain a fluid;
    sealing the sampling vessel with the fluid disposed within the sampling vessel;
    retrieving the sampling vessel having the fluid disposed within the sampling vessel as the obtained sample into one of the plurality of sample containers.

6. The method of claim 1, further comprising
    identifying an additional sampling location to obtain one or more of sediment samples, biological samples, chemical samples, other non-hydrocarbon samples and any combination thereof;
    directing the unmanned vehicle to the identified additional sampling location;
    obtaining one or more samples at the identified additional sampling location;
    obtaining one or more samples at the identified additional sampling location; and
    analysing the obtained sample for geochemical or biological materials.

7. The method of claim 1, wherein obtaining the sample of the target material comprises:
    acquiring one or more images with an imaging module associated with at least one sampling container; and
    retrieving the sampling container as the obtained sample into one of the plurality of sample containers.

8. The method of claim 1, further comprising:
    performing a large pattern search from the potential location, wherein the large pattern search comprises detecting the target material;
    if the target material is detected, performing a sampling pattern search to obtain the sample; and
    if the target material is not detected, determining whether to continue the large pattern search.

9. The method of claim 1, wherein detecting the presence of the target material comprises searching for target material by pumping fluid through a target detection module to identify the target material.

10. The method of claim 1, wherein detecting the presence of the target material comprises searching for the target material by analysing the surface of the body of water to detect certain wavelengths to identify the target material.

11. The method of claim 1, wherein detecting the presence of the target material comprises searching for the target material by:
    deploying an unmanned aerial vehicle above the unmanned vehicle;
    obtaining electromagnetic radiation images with the unmanned aerial vehicle; and
    analysing the infrared and visible light images to identify the target material.

12. The method of claim 1, wherein one or more of the plurality of sample containers is configured to:
    unseal the sample container if target material is detected.

13. The method of claim 12, wherein the sample container is configured to seal the sample container after a set period of time once the sample container has been unsealed.

14. The method of claim 1, further comprising managing the temperature within the one of the one or more sample containers on the unmanned vehicle.

15. The method of claim 14, wherein the temperature is maintained with the range between about 10° C. and about −100° C.

16. The method of claim 1, further comprising deploying a distributed sensor network to identify locations of particular target materials.

17. The method of claim 1, wherein obtaining the sample of the target material comprises:
    passing a fluid through a sampling conduit to interact with a sampling material;
    interrupting the fluid passing through the sampling conduit; and
    using the sampling conduit as the sample.

18. The method of claim 1, wherein obtaining the sample of the target material comprises:
  passing a fluid through a filter;
  passing the fluid through a solid phase extraction module; and
  using the filter and the solid phase extraction module as the sample.

19. The method of claim 1, wherein detecting the presence of the target material comprises:
  pumping a fluid from the body of water through a target measurement device to indicate the presence of the target material; and
  notifying the sampling component to obtain a sample if the target material is present.

20. A marine target identification system comprising:
  an unmanned vehicle having a propulsion component, a communication component, a target detection component, and a sample component, wherein the propulsion component is configured to maneuverer the unmanned vehicle, the target detection component is configured to identify target material, the sample component is configured to obtain one or more samples of a target material, and the communication component is configured to communicate signals associated with the obtained samples, wherein the target material comprises one or more of biological, chemical, hydrocarbon, and any combination thereof, and wherein the unmanned vehicle is one of unmanned surface vehicle and an unmanned airborne vehicle.

21. The system of claim 20, wherein the sample component comprises a sample assembly having a plurality of individual sampling containers.

22. The system of claim 20, wherein one or more of the plurality of individual sampling containers has a sampling vessel that is configured to unseal the sampling vessel to obtain the target material; and seal the sampling vessel with the target material disposed within the sampling vessel.

23. The system of claim 20, wherein the target detection component comprises a target detection module and a pump, wherein the pump is configured to obtain surface compounds and pass the surface compounds to the target detection module to identify the target material.

24. The system of claim 23, wherein the target detection component comprises a receiver configured to receive images; and analyse the images to identify certain wavelengths associated with the target material.

25. The system of claim 20, wherein the unmanned vehicle has a camera configured to obtain one or more images as one or more samples are obtained.

26. The system of claim 20, further comprising a deployment unmanned vehicle having a deployment propulsion component, a deployment communication component, a sample deployment component, and a deployment measurement component, wherein the deployment propulsion component is configured to maneuverer the deployment unmanned vehicle, the deployment measurement component is configured to identify the target material, the sample deployment component is configured to deploy a sample container into the identified target material, and the deployment communication component is configured to communicate signals associated with the operation of the deployment unmanned vehicle.

27. The system of claim 26, wherein the sample container comprises a canister having the sampling material disposed within the canister.

28. The system of claim 27, wherein the sample component is configured to retrieve the sample container.

29. The system of claim 20, wherein the sample container is configured to: unseal the sample container to provide interaction between the sampling material and the target material in a body of water when the target material is detected.

30. The system of claim 29, wherein the sample container is configured to seal the sample material within the sample container after a set period of time once the sample container has been unsealed.

31. The system of claim 20, further comprising a storage component disposed on the unmanned vehicle and configured to maintain the temperature within the sampling container within a specified range.

32. The system of claim 31, wherein the temperature is maintained within the range between about 10° C. and about −100° C.

33. The system of claim 21, further comprising a distributed sensor network configured to identify locations of target materials and to communicate the identified locations to the unmanned vehicle.

34. The system of claim 20, wherein one or more of the plurality of individual sampling containers comprises a sampling conduit configured to pass a fluid from the body of water through a sampling material within the sampling conduit.

35. The system of claim 20, wherein one or more of the plurality of individual sampling containers comprises a solid phase extraction module and a filter, wherein the filter is configured to pass a fluid through a filter to remove solids and the solid phase extraction module is configured to pass a fluid through the solid phase extraction material within the solid phase extraction module to interact with the target material.

* * * * *